US006982147B2

(12) United States Patent
Erikson

(10) Patent No.: US 6,982,147 B2
(45) Date of Patent: Jan. 3, 2006

(54) APPARATUS FOR ASSAYING BIOPOLYMER BINDING BY MEANS OF MULTIPLE MEASUREMENTS UNDER VARIED CONDITIONS

(75) Inventor: Glen H. Erikson, Providenciales (TC)

(73) Assignee: Ingeneus Corporation, Bridgetown (BB)

( * ) Notice: Subject to any disclaimer, the term of this patent is extended or adjusted under 35 U.S.C. 154(b) by 0 days.

(21) Appl. No.: 10/120,092

(22) Filed: Apr. 10, 2002

(65) Prior Publication Data

US 2002/0123066 A1 Sep. 5, 2002

Related U.S. Application Data

(63) Continuation-in-part of application No. 09/911,042, filed on Jul. 23, 2001, which is a continuation-in-part of application No. 09/490,273, filed on Jan. 24, 2000, now Pat. No. 6,265,170.

(51) Int. Cl.

| | |
|---|---|
| *C12Q 1/68* | (2006.01) |
| *C12N 15/00* | (2006.01) |
| *C12N 15/63* | (2006.01) |
| *C12N 1/20* | (2006.01) |
| *C07H 21/04* | (2006.01) |

(52) U.S. Cl. .................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search .................... 435/6, 435/91.1, 91.2, 70.1, 320.1; 536/24.3, 23.4; 935/6; 436/518; 530/350; 356/344, 417; 204/299
See application file for complete search history.

(56) References Cited

U.S. PATENT DOCUMENTS

| | | | | |
|---|---|---|---|---|
| 4,220,450 | A | 9/1980 | Maggio | |
| 4,876,187 | A | 10/1989 | Duck et al. | |
| 4,881,812 | A | * 11/1989 | Ohkubo | 356/344 |
| 4,963,477 | A | 10/1990 | Tchen | |
| 5,011,769 | A | 4/1991 | Duck et al. | |
| 5,332,659 | A | 7/1994 | Kidwell | |
| 5,381,224 | A | 1/1995 | Dixon et al. | |
| 5,403,711 | A | 4/1995 | Walder et al. | |
| 5,532,873 | A | 7/1996 | Dixon et al. | |
| 5,538,848 | A | 7/1996 | Livak et al. | |
| 5,539,082 | A | 7/1996 | Nielsen et al. | |
| 5,558,998 | A | 9/1996 | Hammond et al. | |
| 5,660,988 | A | 8/1997 | Duck et al. | |
| 5,674,698 | A | 10/1997 | Zarling et al. | |
| 5,705,346 | A | 1/1998 | Okamoto et al. | |
| 5,707,801 | A | 1/1998 | Bresser et al. | |
| 5,731,146 | A | 3/1998 | Duck et al. | |
| 5,760,951 | A | 6/1998 | Dixon et al. | |
| 5,783,063 | A | 7/1998 | Clarkson et al. | |

(Continued)

FOREIGN PATENT DOCUMENTS

| | | | |
|---|---|---|---|
| EP | WO 99/45595 | * | 9/1999 |
| GB | 2333359 | A | 7/1999 |
| GB | 2338301 | A | 12/1999 |
| WO | WO 95/01370 | A1 | 1/1995 |
| WO | WO 97/45539 | A1 | 12/1997 |
| WO | WO 99/67628 | A1 | 12/1999 |
| WO | WO 00/20633 | A1 | 4/2000 |
| WO | WO 00 75792 | | 12/2000 |

OTHER PUBLICATIONS

Abstract of JP 5237000, Yoshitami (Sep. 17, 1993).
Abstract of Giese, *J. Biomolecular Structure & Dynamics* (Jun., 2000).
Baran et al., *Nucleic Acids Research* 25:297–303 (1997).
Bohmann et al., *Science*, 238:1386–1392 (Dec. 1987).
Carlsson et al., 380 *Nature* 207 (Mar. 21, 1996).
Chan et al., *J. Mol. Med.* 75 Issue 4:267–282 (1997).
Dalrymple et al., *Nucleic Acids Research*, vol. 13, No. 21, pp. 7865–7879 (1985).
Drozdov–Tikhomirov et al., *J. Biomolecular Structure & Dynamics*, vol. 19, No. 2, pp. 279–284 (2001).
Durland et al., *Biochemistry*, 30:9246–9255 (1991).
Egholm et al., 365 *Nature* 566 (Oct. 7, 1993).
Floris et al., 260 *Eur. J. Biochem.* 801–809 (1999).
Giese et al., *Nature* 412, p. 318 (Jul. 19, 2001).
Hill et al., *Methods in Enzymology*, 278:390–416 (1997).
Johansen and Jacobsen, *J Biomol Struct Dyn*, 16(2):205–22 (Oct. 1998) (Abstract).
Kadonaga et al., *Cell*, 51:1079–1090 (Dec. 24, 1987).
Kukreti et al. 25 *Nucleic Acids Research* 4264–4270 (1997).
Marsh et al., *Nucleic Acids Research*, 23;696–700 (1995).
Marsh et al., *Biochemistry* 33:10718–10724 (1994).
Mazumder et al., *Biochemistry* 35:13762–13771 (1996).
Porath, et al., 403 *Nature* 635 (Feb. 10, 2000).
Sen et al., *Nature* 334:364–366 (1988).
Sen et al., *Biochemistry* 31:65–70 (1992).
Sturm et al., *Genes & Development*, 2:1582–1599 (1988).
Tomac et al., 118 *J. Am. Chem. Soc.* 5544–5552 (1996).
Watson, James, "A Personal Account of the Discovery of the Structure of DNA," (1968).
Williamson et al., *Cell* 59:871–880 (Dec. 1, 1989).
Wilson et al., *Cell*, 74:115–126 (Jul. 16, 1993).
Zhurkin et al., *J. Mol. Biol.*, vol. 239, 181–200 (1994).

(Continued)

*Primary Examiner*—Jeffrey Fredman
*Assistant Examiner*—Arun Chakrabarti
(74) *Attorney, Agent, or Firm*—Caesar, Rivise, Bernstein, Cohen & Pokotilow, Ltd.

(57) ABSTRACT

An apparatus for assaying specific binding of a probe to a target, includes: a sample support; a light source; an optical train; a light detector; an electricity source; an electrical property detector; and a data analysis device adapted to: (a) compare an optical determination of binding with an electrical determination of binding, or (b) compare a pre-electrification determination of binding with a post-electrification determination of binding.

19 Claims, 11 Drawing Sheets

U.S. PATENT DOCUMENTS

| | | | | |
|---|---|---|---|---|
| 5,800,984 | A | | 9/1998 | Vary |
| 5,800,992 | A | | 9/1998 | Fodor et al. |
| 5,814,447 | A | | 9/1998 | Ishiguro et al. |
| 5,814,516 | A | | 9/1998 | Vo-Dinh |
| 5,824,477 | A | | 10/1998 | Stanley |
| 5,824,557 | A | | 10/1998 | Burke et al. |
| 5,846,729 | A | | 12/1998 | Wu et al. |
| 5,861,124 | A | | 1/1999 | Hosoi et al. |
| 5,874,213 | A | | 2/1999 | Cummins et al. |
| 5,874,555 | A | | 2/1999 | Dervan et al. |
| 5,888,739 | A | | 3/1999 | Pitner et al. |
| 5,912,332 | A | | 6/1999 | Agrawal et al. |
| 5,948,897 | A | | 9/1999 | Sen et al. |
| 6,013,442 | A | | 1/2000 | Kolesar et al. |
| 6,017,709 | A | | 1/2000 | Hardin et al. |
| 6,027,880 | A | | 2/2000 | Cronin et al. |
| 6,046,004 | A | | 4/2000 | Wu et al. |
| 6,048,690 | A | | 4/2000 | Heller et al. |
| 6,051,380 | A | | 4/2000 | Sosnowski et al. |
| 6,060,242 | A | | 5/2000 | Nie et al. |
| 6,096,496 | A | * | 8/2000 | Frankel ......................... 435/4 |
| 6,107,078 | A | | 8/2000 | Keese et al. |
| 6,117,657 | A | | 9/2000 | Usman et al. |
| 6,251,591 | B1 | | 6/2001 | Wu et al. |
| 6,255,050 | B1 | | 7/2001 | Nie et al. |
| 6,255,469 | B1 | | 7/2001 | Seeman et al. |
| 6,265,170 | B1 | | 7/2001 | Picard et al. |
| 6,287,772 | B1 | | 9/2001 | Stefano et al. |
| 6,294,333 | B1 | | 9/2001 | Daksis et al. |
| 6,306,584 | B1 | * | 10/2001 | Bamdad ........................ 435/6 |
| 6,312,925 | B1 | | 11/2001 | Meyer et al. |
| 6,391,624 | B1 | | 5/2002 | Megerle |
| 6,613,524 | B1 | | 9/2003 | Erikson |
| 6,664,071 | B1 | | 12/2003 | Windhab et al. |
| 2001/0021534 | A1 | | 9/2001 | Wohlstadter et al. |
| 2001/0051113 | A1 | | 12/2001 | Juncosa et al. |
| 2002/0094531 | A1 | | 7/2002 | Zenhausern |

OTHER PUBLICATIONS

Khrapko et al., "Identification of point mutations in mixtures by capillary electrophoresis hybridization," *Nucleic Acid Research*, vol. 26, No. 24, pp. 5738–5740 (1998).

Cheng et al., "Preparation and hybridization analysis of DNA/RNA from E. Coli on microfabricated bioelectronic chips," *Nature Biotechnology*, vol. 16, pp. 541–546 (1998).

* cited by examiner

Figure 1A (1V; antiparallel PNA probe)
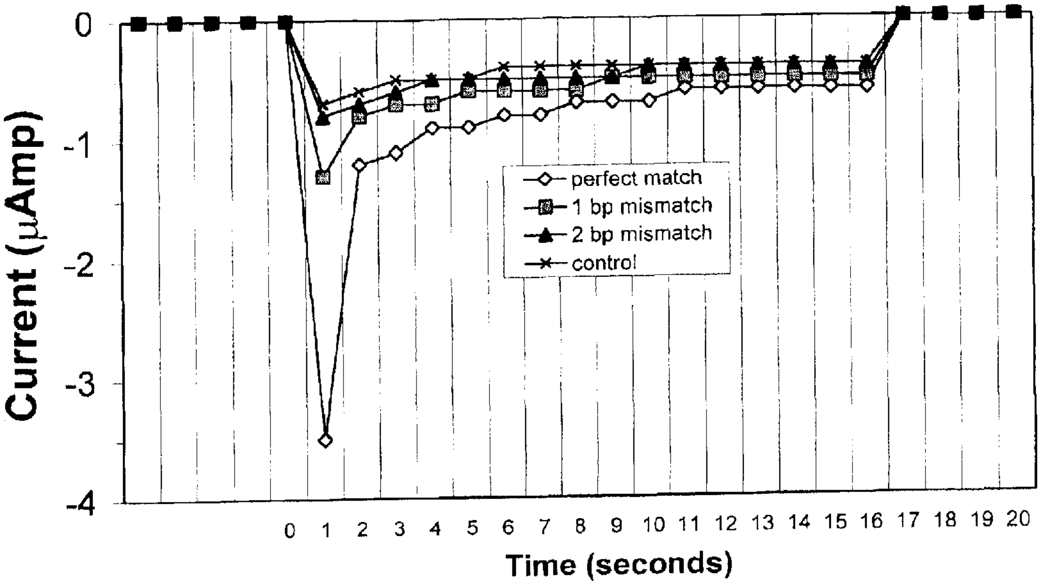
Figure 1B (5V; antiparallel PNA probe)
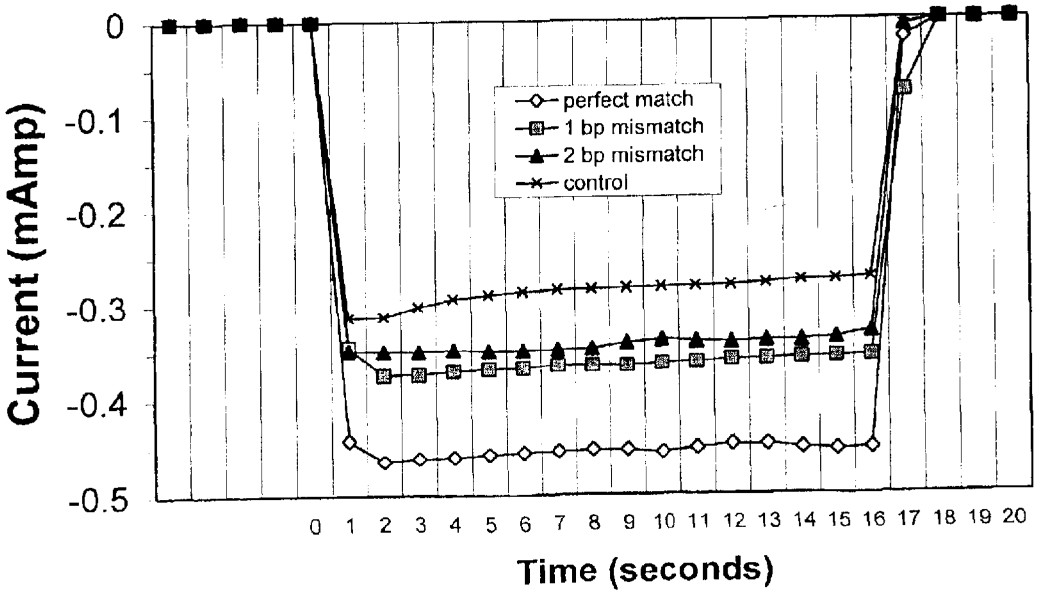

Figure 1C (1V; antiparallel PNA probe)
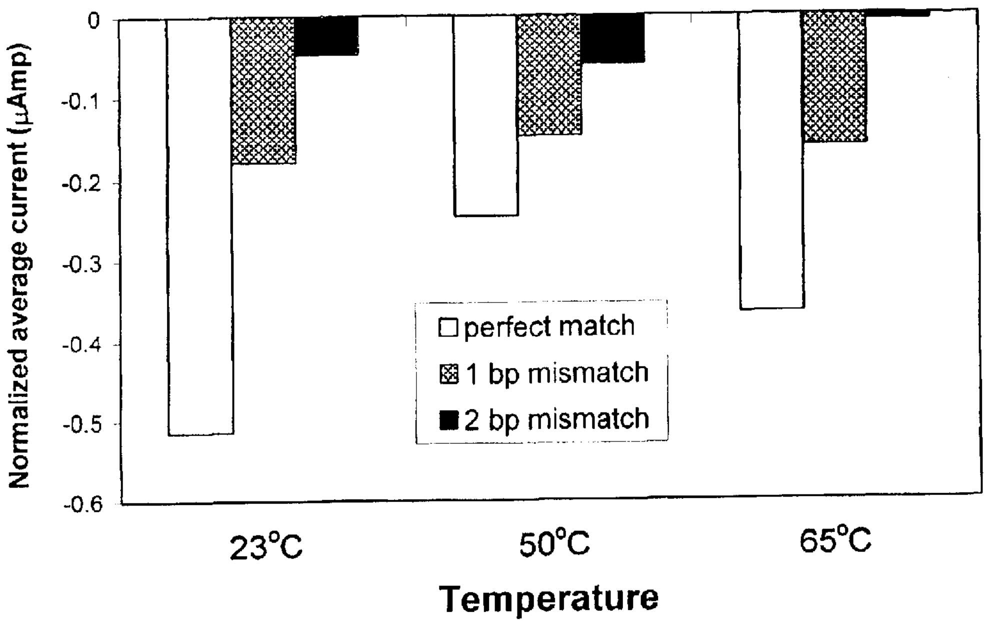
Figure 1D (5V; antiparallel PNA probe)
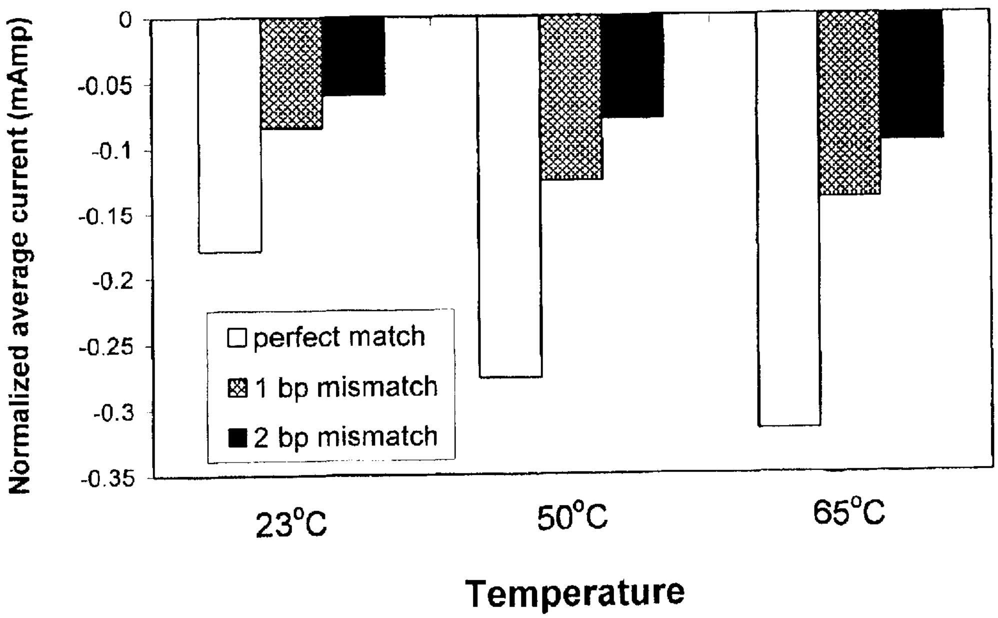

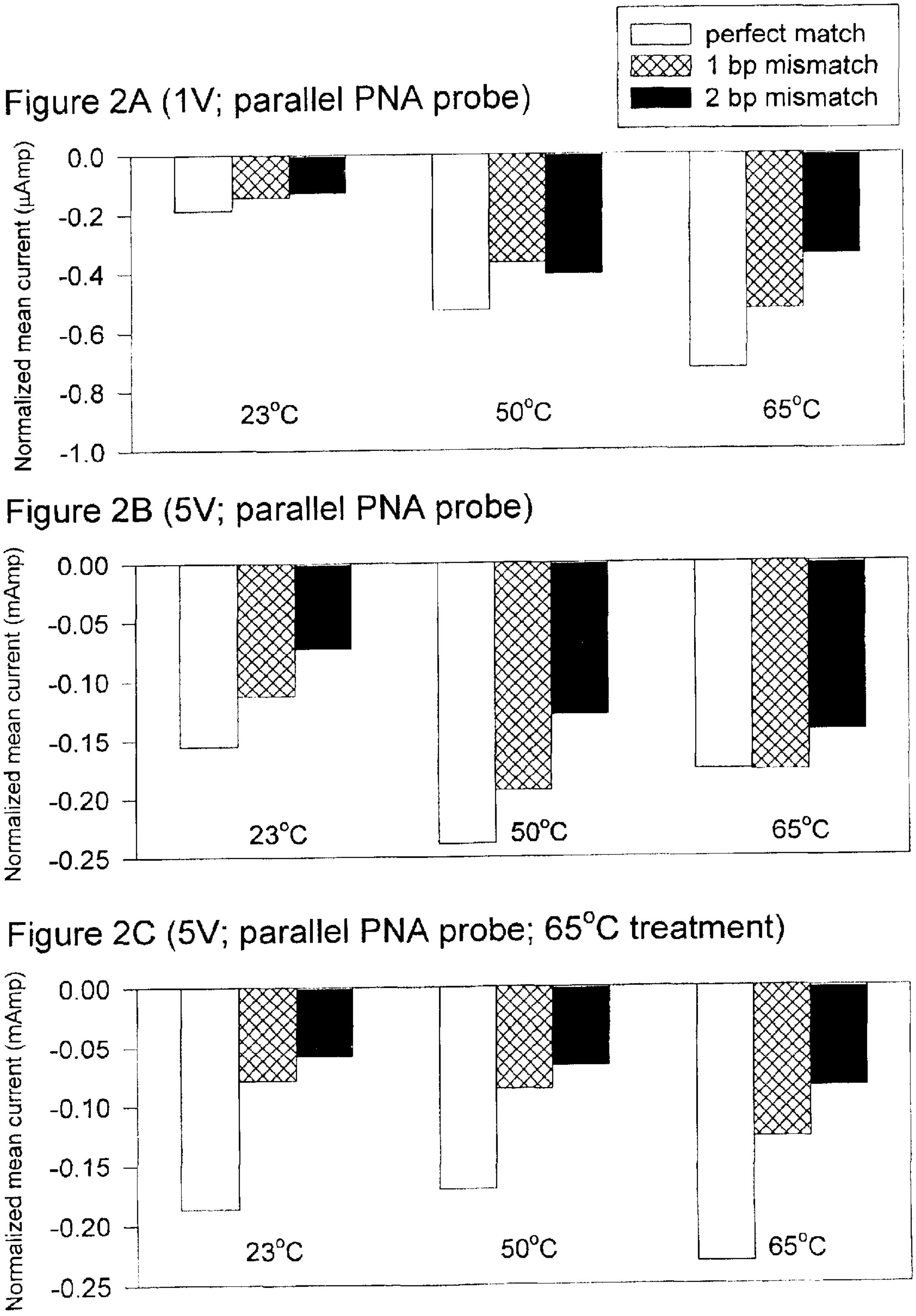
perfect match
1 bp mismatch
2 bp mismatch
Figure 2A (1V; parallel PNA probe)
Normalized mean current (μAmp)
0.0
-0.2
-0.4
-0.6
-0.8
-1.0
23°C
50°C
65°C
Figure 2B (5V; parallel PNA probe)
Normalized mean current (mAmp)
0.00
-0.05
-0.10
-0.15
-0.20
-0.25
23°C
50°C
65°C
Figure 2C (5V; parallel PNA probe; 65°C treatment)
Normalized mean current (mAmp)
0.00
-0.05
-0.10
-0.15
-0.20
-0.25
23°C
50°C
65°C

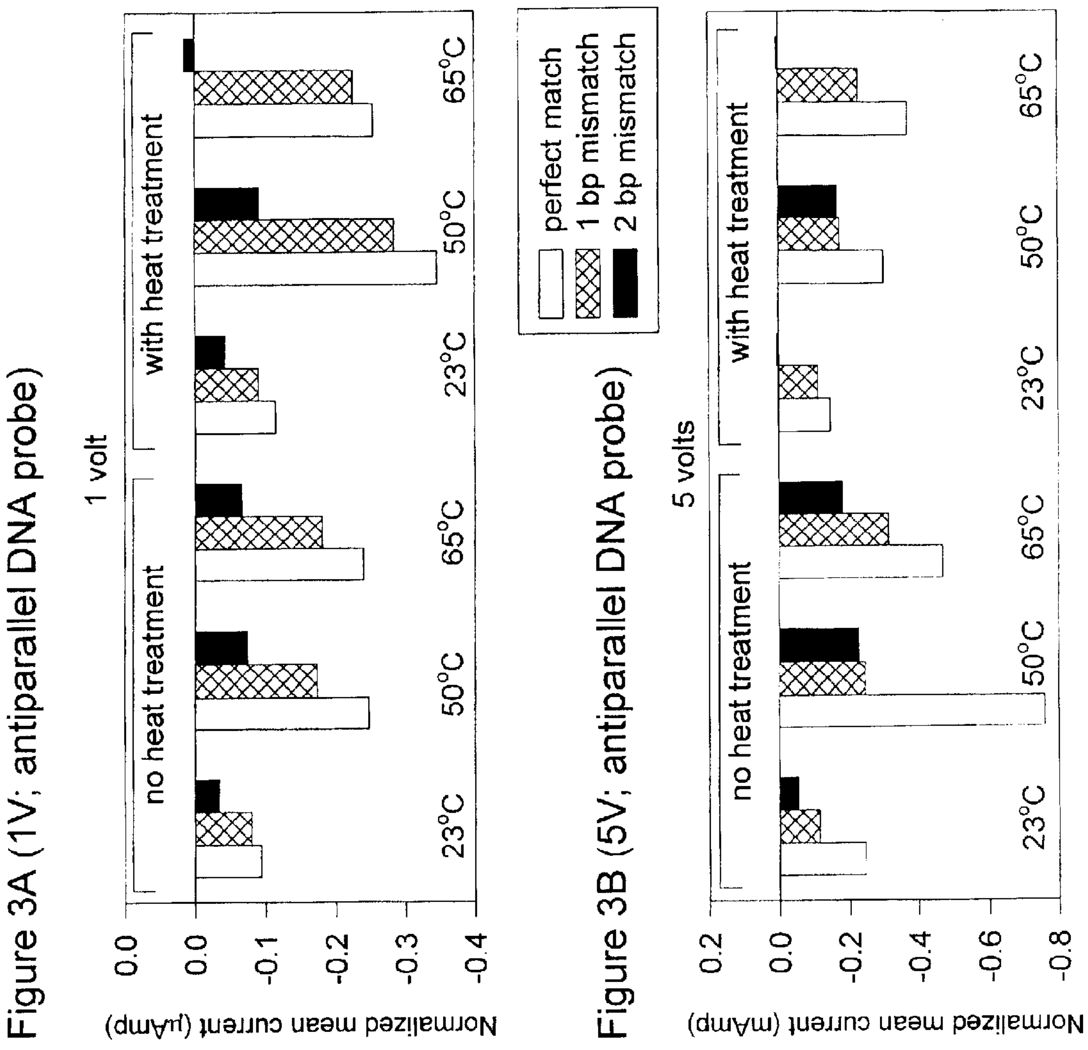
Figure 3A (1V; antiparallel DNA probe)
Figure 3B (5V; antiparallel DNA probe)

Figure 4 (5V; DNA probe with attached acridine)
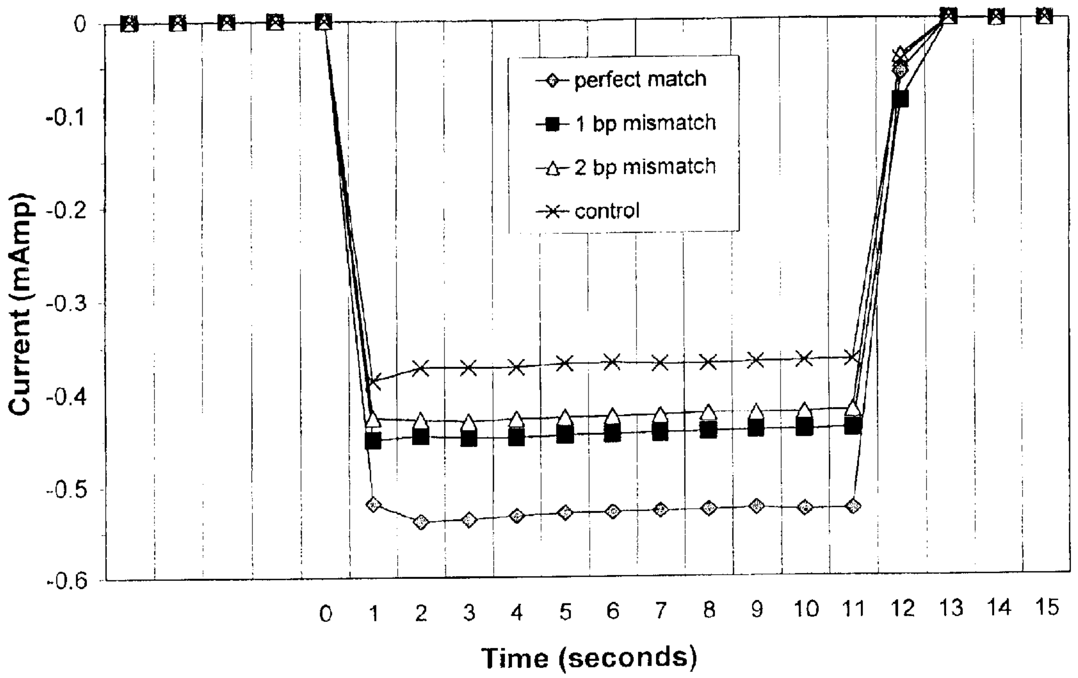

Figure 5A (PNA:DNA perfect match; 65°C)
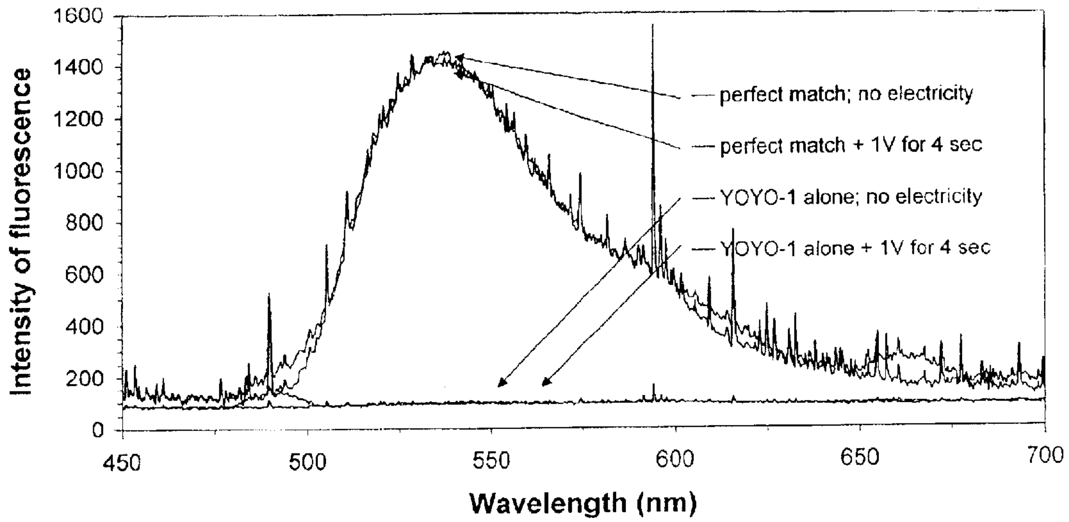
Figure 5B (PNA:DNA 1bp mismatch; 65°C)
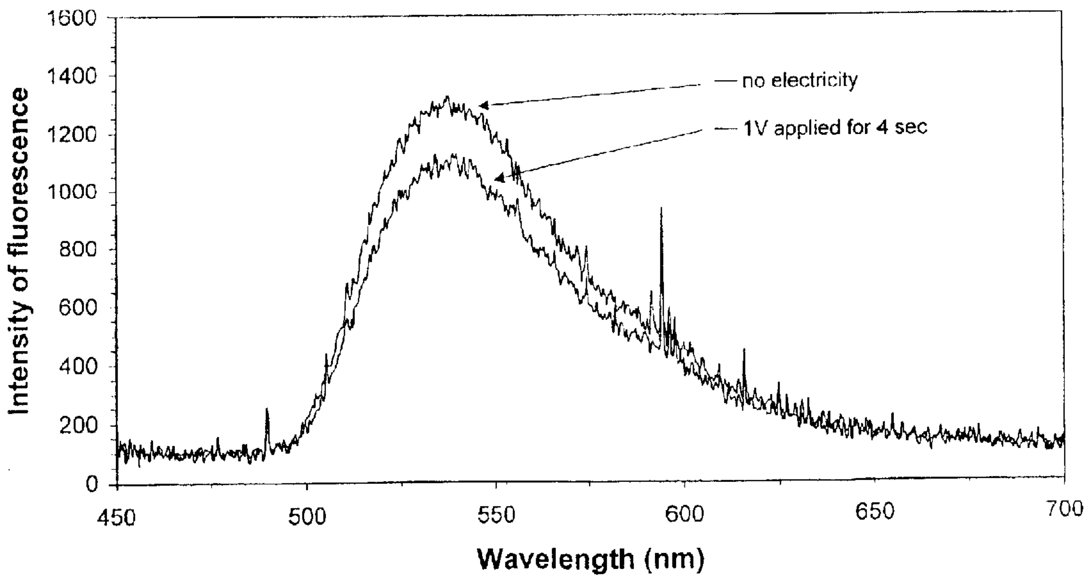

Figure 5C (PNA:DNA 2bp mismatch; 65°C)
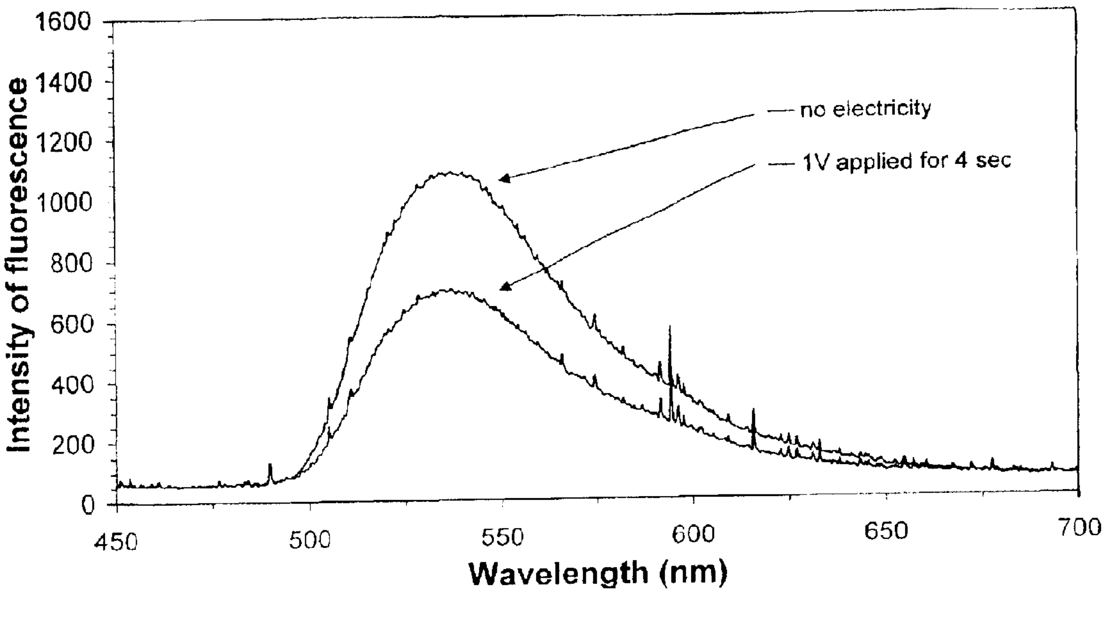

Figure 6. ssPNA:dsDNA hybridization at 23°C without prior denaturation
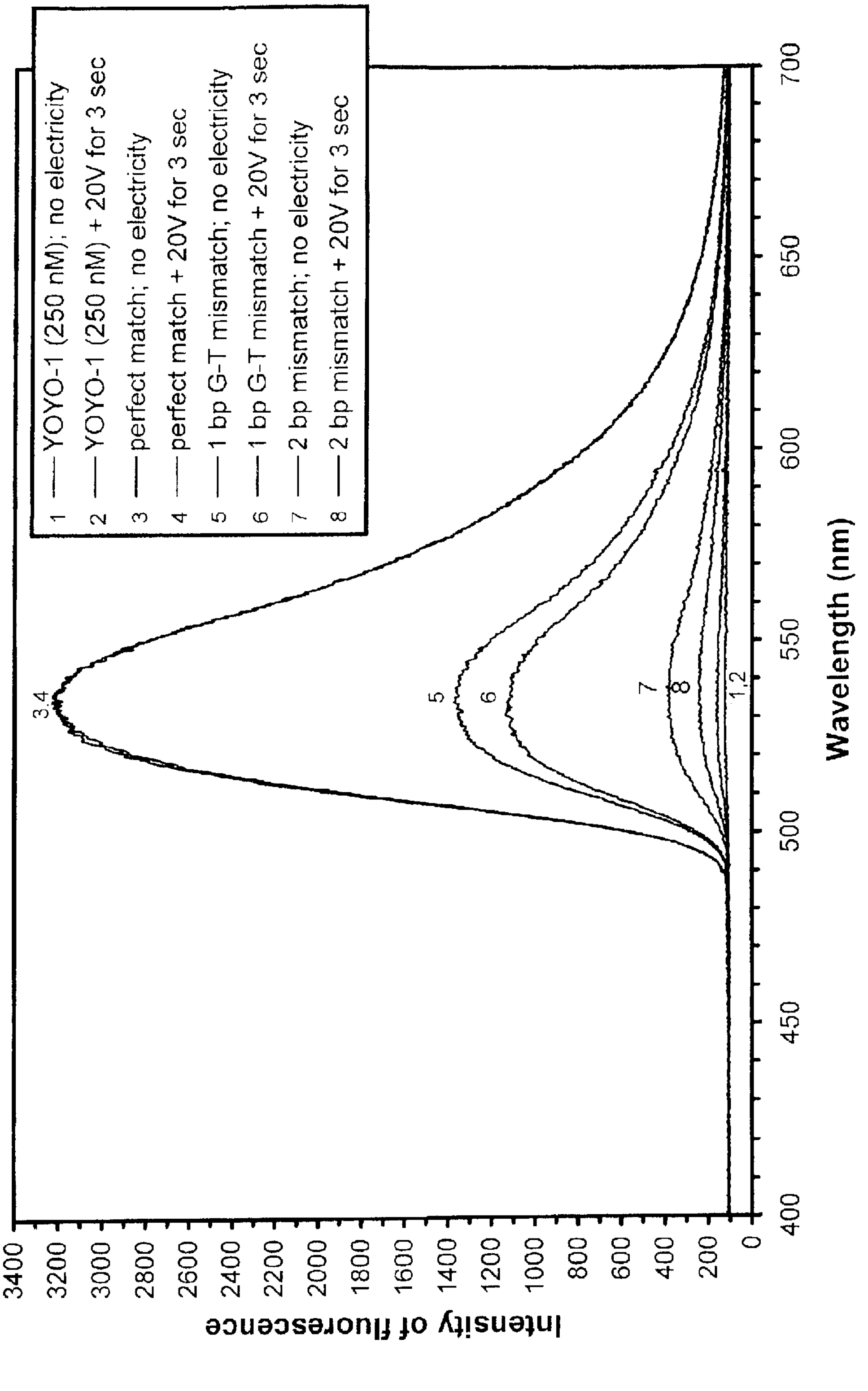

APPARATUS FOR ASSAYING BIOPOLYMER BINDING BY MEANS OF MULTIPLE MEASUREMENTS UNDER VARIED CONDITIONS

BACKGROUND OF THE INVENTION

1. Field of Invention

The invention relates to apparatus for assaying biopolymer binding, and more particularly to apparatus for assaying binding of probes and targets containing nucleobases and/or amino acids.

2. Description of Related Art

It has been understood for a number of years that biological molecules can be isolated and characterized through the application of an electric field to a sample.

Electrophoresis is perhaps the most well-known example of an isolation and characterization technique based on the influence of electric fields on biological molecules. In gel electrophoresis, a uniform matrix or gel is formed of, for example, polyacrylamide, to which an electric field is applied. Mixtures applied to one end of the gel will migrate through the gel according to their size and interaction with the electric field. Mobility is dependent upon the unique characteristics of the substance such as conformation, size and charge. Mobilities can be influenced by altering pore sizes of the gel, such as by altering the concentration of the acrylamide, bis-acrylamide, agarose or cross-linking agent, or by formation of a concentration or pH gradient, or by altering the composition of the buffer (pH, SDS, DOC, glycine, salt). One- and two-dimensional gel electrophoresis are fairly routine procedures in most research laboratories. Target substances can be purified by passage through and/or physical extraction from the gel.

A more recently developed process in which an electric field is applied to a biological sample is disclosed in U.S. Pat. No. 5,824,477 to Stanley. The Stanley patent discloses a process for detecting the presence or absence of a predetermined nucleic acid sequence in a sample. The process comprises: (a) denaturing a sample double-stranded nucleic acid by means of a voltage applied to the sample in a solution by means of an electrode; (b) hybridizing the denatured nucleic acid with an oligonucleotide probe for the sequence; and (c) determining whether the hybridization has occurred. The Stanley patent discloses the application of an electric field to the sample to be assayed for the limited purpose of denaturing the target sequence.

A more well-known type of hybridization assay is based on the use of fluorescent marking agents. In their most basic form, fluorescent intensity-based assays have typically comprised contacting a target with a fluorophore-containing probe, removing any unbound probe from bound probe, and detecting fluorescence in the washed sample. Homogeneous assays improve upon such basic assays, in that the former do not require a washing step or the provision of a non-liquid phase support.

Some assays have employed intercalating fluorophores to detect nucleic acid hybridization, based on the ability of such fluorophores to bind between strands of nucleic acid in a hybridization complex.

For example, U.S. Pat. No. 5,824,557 to Burke et al. discloses a method and kit for detecting and quantitating nucleic acid molecules. A preferred embodiment relies on the intercalation of a dye into a double-stranded nucleic acid helix or single-stranded nucleic acid. The dye fluoresces after intercalation and the intensity is a direct measurement of the amount of nucleic acid present in the sample. While the method of Burke et al. is purported to be useful for measuring the amount of nucleic acid in a sample, the non-specific binding between intercalator and nucleic acid upon which the method is based renders the method impractical for detecting specific binding, particularly under conditions where non-target nucleic acid duplexes are present.

U.S. Pat. No. 5,814,447 to Ishiguro et al. discloses an assay which is purported to improve upon assays that rely on non-specific interaction between intercalating agents and nucleic acid duplexes, such as Burke et al. and an earlier assay described by Ishiguro et al. in Japanese Patent Public Disclosure No. 237000/1993. The earlier development comprised adding an intercalating fluorochrome having a tendency to exhibit increased intensity of fluorescence when intercalated to a sample solution before a specific region of a target nucleic acid was amplified by PCR, and measuring the intensity of fluorescence from the reaction solution at given time intervals to detect and quantitate the target nucleic acid before amplification. The '447 patent attempted to improve upon the earlier development by providing an assay having improved specificity, characterized in that the probe is a single-stranded oligonucleotide labeled with an intercalating fluorochrome which is to be intercalated into a complementary binding portion between a target nucleic acid and a single-stranded oligonucleotide probe.

In the ongoing search for more sensitive, accurate and rapid assay techniques, one research group developed an assay comprising analyzing the effects of an electric field on the fluorescent intensity of nucleic acid hybridization duplexes. See U.S. patent application Ser. No. 08/807,901, filed Feb. 27, 1997 and U.S. Pat. No. 6,060,242. The researchers indicated that the fluorescent intensity of a one base-pair mismatched duplex differed from that of a perfectly matched duplex. Thus, the applications purport to disclose a method for detecting a nucleotide sequence, wherein an electric field is applied to a liquid medium prior to or concurrently with a detecting step, and a change in an intensity of a fluorescent emission as a function of the electric field is detected as an indication of whether the probe is hybridized to a completely complementary nucleotide sequence or an incompletely complementary nucleotide sequence.

U.S. Pat. No. 6,265,170 and U.S. patent application Ser. No. 09/911,047, filed Jul. 23, 2001, disclose a simple, highly sensitive, effective and rapid method for analyzing interaction between nucleic acids and/or nucleic acid analogs.

Devices for detecting fluorescently marked targets are known. For example, U.S. Pat. Nos. 5,760,951, 5,532,873 and 5,381,224 to Dixon et al. disclose scanning laser imaging systems, which can be used to analyze biological samples that fluoresce when excited by laser irradiation.

U.S. Pat. No. 6,141,096 to Stern et al. discloses an apparatus for detecting fluorescently marked regions on a surface of a substrate.

Despite the foregoing developments, it is still desired to provide a novel apparatus for assaying binding of probes and targets containing nucleobases and/or amino acids.

It is further desired to provide such a novel apparatus, wherein binding is assayed by measuring optical and/or electrical properties of a sample.

All references cited herein are incorporated herein by reference in their entireties.

BRIEF SUMMARY OF THE INVENTION

Accordingly, the invention provides an apparatus for assaying specific binding of a probe to a target, said apparatus comprising:

- a sample support for supporting a sample containing the probe and the target;
- a light source for irradiating the sample;
- an optical train for conveying light from the light source to the sample;
- a light detector for detecting light emitted from the sample;
- an electricity source for providing an electric charge through the sample;
- an electrical property detector for detecting an electrical property of the sample; and
- a data analysis device in communication with the light detector and the electrical property detector, wherein the data analysis device is adapted to:
  - (a) (1) produce an optical determination of probe-target binding as a function of light emitted from the sample,
    - (2) produce an electrical determination of probe-target binding as a function of the electrical property, and
    - (3) compare the optical determination with the electrical determination to assay specific binding of the probe to the target; or
  - (b) (1) produce a pre-electrification determination of probe-target binding as a function of light emitted from the sample prior to providing the electric charge through the sample,
    - (2) produce a post-electrification determination of probe-target binding as a function of light emitted from the sample concurrent with and/or subsequent to providing the electric charge through the sample, and
    - (3) compare the pre-electrification determination with the post-electrification determination to assay specific binding of the probe to the target.

BRIEF DESCRIPTION OF SEVERAL VIEWS OF THE DRAWINGS

The invention will be described in conjunction with the following drawings in which like reference numerals designate like elements and wherein:

FIGS. 1A and 1B are graphs of current as a function of time and complementarity;

FIGS. 1C and 1D are graphs of current as a function of temperature and complementarity;

FIGS. 2A, 2B, 2C, 3A and 3B are graphs of current as a function of temperature, complementarity and additional factors;

FIG. 4 is a graph of current as a function of time and complementarity;

FIGS. 5A, 5B, 5C and 6 are fluorescent intensity spectra;

DETAILED DESCRIPTION OF THE INVENTION

Figure 7:
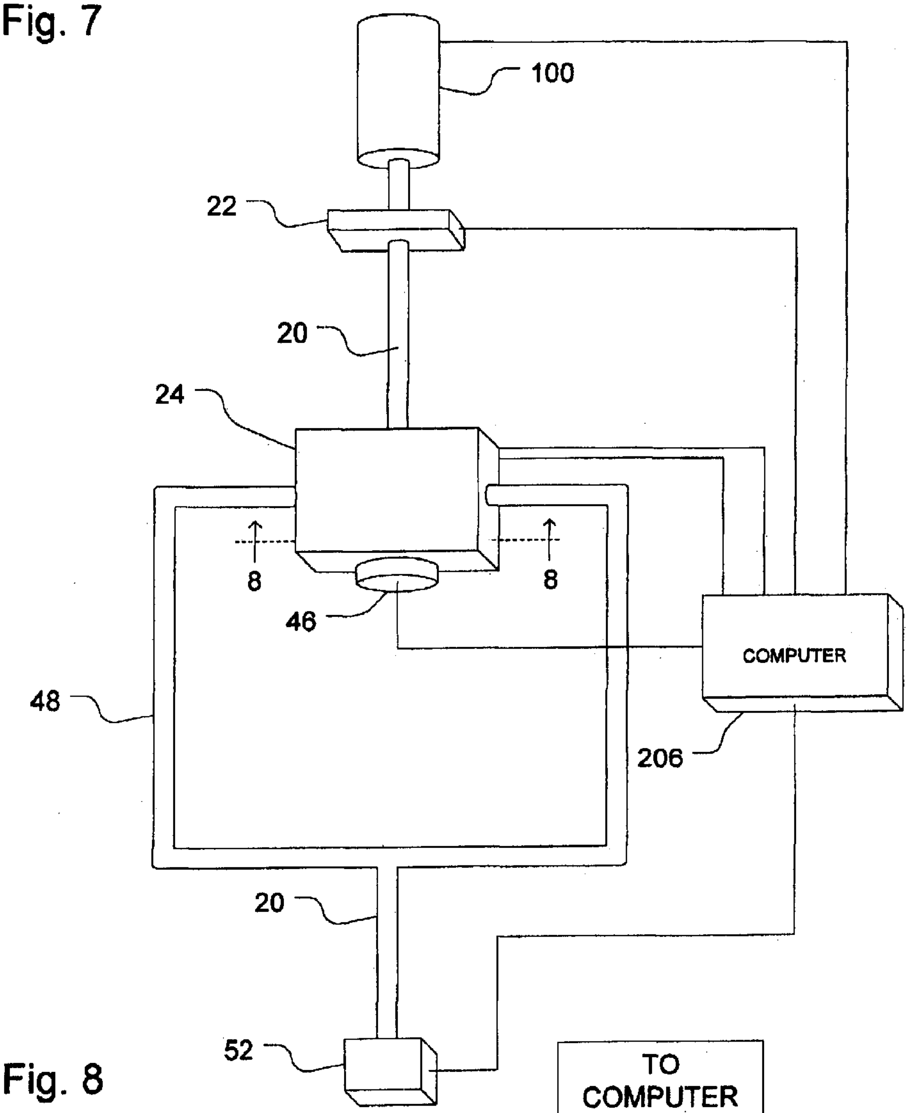
FIG. 7 is an overhead schematic view of an embodiment of an apparatus of the invention.

The invention provides a rapid, sensitive, environmentally friendly, and safe system for assaying binding between a target and a probe, wherein the target comprises a nucleic acid sequence or a nucleic acid analog sequence and the probe comprises a nucleic acid sequence or a nucleic acid analog sequence. The system of the invention is also suitable for assaying binding between a target and a probe, wherein the target and/or the probe comprises an amino acid sequence. Thus, the invention is suitable for assaying binding of biopolymers, which as used herein, means a sequence containing at least two amino acids, amino acid analogs, nucleic acids, nucleic acid analogs and/or combinations thereof.

Unlike certain prior art systems, the invention not only detects the presence of specific binding, but also provides qualitative and quantitative information regarding the nature of binding between a probe and target. Thus, in embodiments comprising nucleobase to nucleobase binding assays, the invention enables the practitioner to distinguish among a perfect match, a one base pair mismatch, a two base pair mismatch, a three base pair mismatch, a one base pair deletion, a two base pair deletion and a three base pair deletion.

Embodiments of the invention comprise calibrating the measured signal (e.g., electric current and/or fluorescent intensity) for a first probe-target mixture against the same type of signal exhibited by other probes combined with the same target, wherein each of the other probes differs from the first probe by at least one base.

In certain embodiments, a low voltage is applied to the sample prior to or concurrent with measuring said signal. Generally, the voltage is selected such that it is high enough to destabilize imperfectly matched hybridization partners but not so high as to destabilize perfectly matched hybridization partners. In certain preferred embodiments, the voltage is about 1 V to about 27 V.

A calibration curve can be generated, wherein the magnitude of the measured signal (e.g., electric current and/or fluorescent intensity) is a function of the binding affinity between the target and probe. As the binding affinity between the target and a plurality of different probes varies with the number of mismatched bases in nucleobase-nucleobase assays, the nature of the mismatch (A-G vs. A-C vs. T-G vs. T-C, etc.), the location of the mismatch(es) within the hybridization complex, etc., the assay of the invention can be used to sequence the target.

The signal measured can be, e.g., electrical conductance. In such embodiments, the binding affinity between the probe and target is directly correlated with the magnitude of the signal. That is, the electrical conductance increases along with the extent of matching between the probe and target, preferably over a range inclusive of 0–2 mismatches and/or deletions, more preferably over a range inclusive of 0–3 mismatches and/or deletions.

In other embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Thus, the fluorescent intensity generated by intercalating agents is directly correlated with probe-target binding affinity, whereas the intensity of embodiments employing non-intercalating fluorophores covalently bound to the probe is inversely correlated with probe-target binding affinity. The fluorescent intensity increases (or decreases for non-intercalators) along with the extent of matching between the probe and target, preferably over a range inclusive of 0–2 mismatches and/or deletions, more preferably over a range inclusive of 0–3 mismatches and/or deletions.

Although the inventors have previously disclosed the advantages of fluorescent intensity assays for analyzing hybridization of nucleobase-containing sequences (see U.S. patent application Ser. No. 09/468,679, filed Dec. 21, 1999) and the advantages of fluorescent intensity assays for analyzing peptide:nucleic acid binding (see U.S. Pat. No. 6,294,333) and peptide:peptide binding (see U.S. patent application Ser. No. 09/344,525, filed Jun. 25, 1999), the application of an electric field to the sample appears to increase the resolution of the assay, as shown in Example 6 below.

Moreover, in particularly preferred embodiments of the invention, the assay comprises measuring at least two signals of the sample. The first signal is preferably fluorescent intensity and the second signal is preferably selected from several electrical conductance measurements (or vice versa).

In the preferred multiple measurement embodiments, the first signal can be the same as or different from the second signal. When the first and second signals measured are the same, the second signal can be calibrated against the first signal and/or against the same reference signal(s) used to calibrate the first signal. In addition, at least one condition-altering stimulus is preferably applied to the test sample after the first signal is measured and before the second signal is measured. The stimulus is preferably sufficient to measurably change binding, as indicated by at least one signal. In nucleobase-nucleobase binding assays of the invention, the stimulus is preferably sufficient to significantly affect imperfectly complementary hybridization between the probe and the target and insufficient to significantly affect perfectly complementary hybridization between the probe and the target.

In certain embodiments of the invention, at least one stimulus is applied once or a plurality of times. The stimulus can be continuously applied or non-continuously applied. The stimulus can be applied before, during and/or after the detection of signal detection.

Suitable stimuli can be, e.g., photonic radiation (such as laser light) and/or electronic. The signals detected can be, e.g., photonic and/or electronic as well.

For example, in a particularly preferred embodiment of the invention, the first signal measured is pre-electrification fluorescent intensity (i.e., intensity measured before a condition-altering voltage is applied to the test sample) and the second signal measured is post-electrification fluorescent intensity (i.e., intensity measured during or after the condition-altering voltage has been applied to the test sample)

The additional measurements in the foregoing embodiments increase the reliability of the assay and enable immediately retesting suspect results. Inconsistent results achieved by the at least two measurements will typically warrant retesting.

The invention enables quantifying the binding affinity between probe and target. Such information can be valuable for a variety of uses, including designing antisense drugs with optimized binding characteristics.

Unlike prior art methods, the assay of the invention is preferably homogeneous. The assay can be conducted without separating the probe-target complex from the free probe and target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor requirements to be rapidly determined.

The assay can be conducted in e.g., a solution within a well, on an impermeable surface, on a biochip, or in a channel or microchannel. In certain embodiments, it may be useful to employ as a sample support the Patterned Multi-Array Multi-Specific Surface PMAMS for electrochemiluminescent assays disclosed in published U.S. patent application No. 2001/0021534 A1 to Wohlstadter et al. and/or the sample support and associated sample handling devices disclosed in published U.S. patent application No. 2001/0051113 A1 to Juncosa et al.

Moreover, the inventive assay is preferably conducted without providing a signal quenching agent on the target or on the probe.

Preferred embodiments of the invention specifically detect triplex and/or quadruplex hybridization between the probe and the double-stranded target, thus obviating the need to denature the target. Triplex and quadruplex formation and/or stabilization is enhanced by the presence of an intercalating agent in the sample being tested. See, e.g., U.S. patent application Ser. No. 09/885,731, filed Jun. 20, 2001, and U.S. Pat. Application No. 09/909,496, filed Jul. 20, 2001.

Suitable nucleobase-containing probes for use in the inventive assay include, e.g., ssDNA, RNA, PNA and other nucleic acid analogs having uncharged or partially-charged backbones. Although antiparallel probes are preferred in certain embodiments, probes can also be parallel. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 6 to 30 bases are most preferred. However, a plurality of shorter probes can be used to detect a nucleotide sequence having a plurality of non-unique target sequences therein, which combine to uniquely identify the nucleotide sequence. The length of the probe can be selected to match the length of the target.

Suitable amino acid-containing probes can comprise a single amino acid, single amino acid analog, a peptide-like analog, peptidoid, peptidomimetic, peptide, dipeptide, tripeptide, polypeptide, protein or a multi-protein complex.

The invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments of the invention wherein the target comprises amino acids, the target preferably comprises a peptide sequence or a peptide-like analog sequence, such as, e.g., a dipeptide, tripeptide, polypeptide, protein or a multi-protein complex. More preferably, the target is a protein having at least one receptor site for the probe.

In embodiments of the invention wherein the target comprises nucleobases, the targets are preferably 8 to $3.3\times10^9$ base pairs long, and can be single or double-stranded sequences of nucleic acids and/or analogs thereof.

It is preferred that the probe and target be unlabeled, but in alternative embodiments, there is an intercalating agent covalently bound to the probe. In such embodiments, the intercalating agent is preferably bound to the probe at either end.

In other embodiments, the intercalating agent is not covalently bound to the probe, although it can insert itself between the probe and target during the assay, in a sense bonding to the probe in a non-covalent fashion.

Preferred intercalating agents for use in the invention include, e.g., YOYO-1, TOTO-1, ethidium bromide, ethidium homodimer-1, ethidium homodimer-2 and acridine. In general, the intercalating agent is a moiety that is able to intercalate between strands of a duplex, triplex and/or a quadruplex nucleic acid complex. In preferred embodiments, the intercalating agent (or a component thereof) is essentially non-fluorescent in the absence of nucleic acids and fluoresces when intercalated and excited by radiation of an appropriate wavelength, exhibiting a 100-fold to 10,000-fold enhancement of fluorescence when intercalated within a duplex or triplex nucleic acid complex.

In alternative embodiments, the intercalating agent may exhibit a shift in fluorescent wavelength upon intercalation and excitation by radiation of an appropriate wavelength. The exact fluorescent wavelength may depend on the structure of the nucleic acid that is intercalated, for example, DNA vs. RNA, duplex vs. triplex, etc.

The excitation wavelength is selected (by routine experimentation and/or conventional knowledge) to correspond to this excitation maximum for the fluorophore being used, and is preferably 200 to 1000 nm. Intercalating agents are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The inventive assay is extremely sensitive, thereby obviating the need to conduct PCR amplification of the target. For example, in at least the fluorescent intensity embodiments, it is possible to assay a test sample having a volume of about 20 microliters, which contains about 10 femtomoles of target and about 10 femtomoles of probe. Embodiments of the invention are sensitive enough to assay targets at a concentration of $5\times10^{-9}$ M, preferably at a concentration of not more than $5\times10^{-10}$ M. Embodiments of the invention are sensitive enough to employ probes at a concentration of $5\times10^{-9}$ M, preferably at a concentration of not more than $5\times10^{-10}$ M.

Conductivity measurements can distinguish samples having as little as about 1 pmole of probe and 1 pmole of target in 40 microliters. Decreasing the sample volume permits the use of even smaller amounts of probe and target.

It should go without saying that the foregoing values are not intended to suggest that the method cannot detect higher concentrations.

A wide range of intercalator concentrations are tolerated at each concentration of probe and target tested. For example, when $5\times10^{-10}$ M probe and $5\times10^{-10}$ M target are hybridized, the optimal concentration of the intercalator YOYO-1 ranges from 25 nM to 2.5 nM. At a $5\times10^{-8}$ M concentration of both probe and target, the preferred YOYO-1 concentration range is 1000 nM to 100 nM.

The assay is sufficiently sensitive to distinguish a one base-pair mismatched probe-target complex from a two base-pair mismatched probe-target complex, and preferably a two base-pair mismatched probe-target complex from a three base-pair mismatched probe-target complex. Of course, the assay is sufficiently sensitive to distinguish a perfectly matched probe-target complex from any of the above mismatched complexes.

The binding medium can be any conventional medium known to be suitable for preserving nucleotides and/or proteins. See, e.g., Sambrook et al., "Molecular Cloning: A Lab Manual," Vol. 2 (1989). For example, the liquid medium can comprise nucleotides, water, buffers and standard salt concentrations.

Hybridization between complementary bases occurs under a wide variety of conditions having variations in temperature, salt concentration, electrostatic strength, and buffer composition. Examples of these conditions and methods for applying them are known in the art.

It is preferred that hybridization complexes be formed at a temperature of about 15° C. to about 25° C. for about 1 minute to about 5 minutes. Longer reaction times are not required, but incubation for several hours will not adversely affect the hybridization complexes.

It is possible (although unnecessary, particularly for embodiments containing an intercalating agent) to facilitate hybridization in solution by using certain reagents. Preferred examples of these reagents include single stranded binding proteins such as Rec A protein, T4 gene 32 protein, *E. coli* single stranded binding protein, major or minor nucleic acid groove binding proteins, divalent ions, polyvalent ions, viologen and intercalating substances such as ethidium bromide, actinomycin D, psoralen, and angelicin. Such facilitating reagents may prove useful in extreme operating conditions, for example, under abnormal pH levels or extremely high temperatures.

The inventive assay can be used to, e.g., identify accessible regions in folded nucleotide sequences, to determine the number of mismatched base pairs in a hybridization complex, and to map genomes.

In embodiments wherein fluorescent intensity is detected using an intercalating agent, intensity increases with increasing binding affinity between the probe and target. In embodiments wherein fluorescent intensity is detected using a non-intercalating fluorophore, intensity decreases as binding affinity increases between the probe and target. Regardless of whether the fluorophore intercalates or not, the instant method does not require the measurement of the polarization of fluorescence, unlike fluorescent anisotropy methods.

A preferred apparatus for performing the method of the invention includes a light source, an electric source, sample handling means, a photon detector, an electron detector and a data analysis device.

Figure 8:
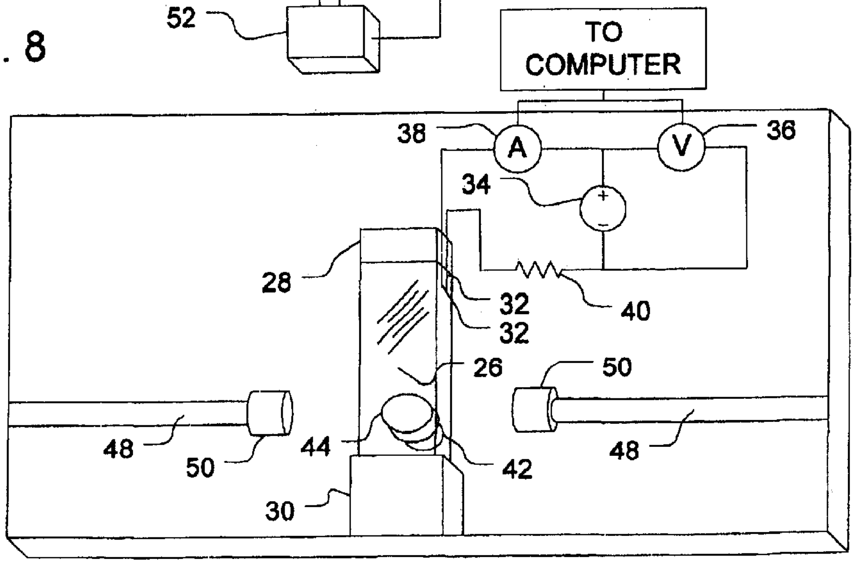
FIG. 8 is a partial cross-sectional view through line 8-8 of FIG. 7.

Referring to FIGS. 7 and 8, a preferred apparatus of the invention includes a laser as light source 100. Non-coherent (or polychromatic) light generation devices are also suitable for use in the invention. Light source 100 is preferably an argon laser that generates a beam having a wavelength of about 488 nm, which in some embodiments may be a model 2017 or model 161C manufactured by Spectra-Physics or a model 170B manufactured by Omnichrome (now Melles Griot). Other lasers, such as diode lasers, helium lasers, dye lasers, titanium sapphire lasers, Nd:YAG lasers or others can also be employed.

Light source 100 emits a beam (not shown in FIG. 7), which is conveyed through optical fiber 20 past shutter 22 and into sample chamber 24. Light source 100 and shutter 22 are preferably controlled by computer 206 (e.g., a PENTIUM 4 based PC) to provide a desired amount of radiation to sample 26 within sample chamber 24. When taking measurements with the apparatus, light emission data collected when the shutter is being opened or closed should be discarded. For example, the data acquisition can be started about 25 milliseconds after opening the shutter and stopped about 25 milliseconds before closing the shutter. A shutter is optionally provided in the embodiments shown in FIGS. 9 and 10.

Sample 26 is placed within sample chamber 24 by, e.g., opening a lid (not shown) of sample chamber 24 and placing sample container 28 within holder 30. Electrodes 32 are placed within sample 26 for purposes of conducting electricity into sample 26 and/or measuring electrical characteristics of sample 26. Electrodes 32 are a part of an electric circuit including voltage source 34, voltmeter 36, ammeter 38 and resistor 40 provided for the purpose of performing the measurements of the electrical characteristics of the sample 26. Voltage source 34 preferably provides direct current, and can be controlled and monitored via computer 206 using voltmeter 36 and ammeter 38. The monitored values, along with the known value of resistor 40, are used by computer 206 to determine the electrical characteristics of sample 26.

After placing sample 26 in sample chamber 24 and immersing electrodes 32 in the sample, the lid of the sample chamber is replaced to minimize the deleterious effects of extraneous light interfering with the method of the invention. Sample chamber 24 is preferably constructed of opaque materials (e.g., black or blackened metal) in a manner intended to seal out extraneous (ambient) light, unless the sample chamber along with other parts of the apparatus are housed within a light-tight housing.

Although the embodiment depicted in FIGS. 7 and 8 is suitable for manual positioning of the sample, it is also within the scope of the invention to provide automated sample handling means. For example, holder 30 and sample container 28 can be provided on a moving substrate, such as a conveyor belt or rotating platter, or manipulated by a robotic arm to convey sample 26 into and out of sample chamber 24.

Likewise, sample container 28, which is shown as a cuvette (preferably quartz) in FIG. 8, can be provided in a form more conducive to automated, high-throughput sample analysis, such as, e.g., microtiter plates and other sample arrays. In such embodiments, it may be more practical to provide electrodes as part of the container, which would complete the electric circuit when the container is properly positioned within the sample chamber. In any case, it is preferred that sample container 28 be constructed from materials that are transparent or translucent at the wavelength(s) of excitation and emission.

After loading sample 26 in sample chamber 24, light is irradiated from optical fiber input 42 through input filter 44 and into sample 26. Input filter 44 is selected to minimize the amount of light passing to the sample (or even entering sample chamber 24) that has a wavelength other than the excitation wavelength for the fluorophore within the sample. Input filter 44 can be a narrow pass filter, a low pass filter or a high pass filter. For example, when YOYO-1 is used as the marking agent in the sample, input filter 44 can comprise a low pass filter that prevents the emission of light from optical fiber input 42 having a wavelength greater than about 500 nm. Since YOYO-1 has a maximum fluorescent intensity emission at about 536 nm, the low pass filter prevents any light from optical fiber input 42 of similar wavelength from erroneously inflating the detected amount of light emitted by YOYO-1. Of course, a narrow pass filter or a combination of a high pass filter and a low pass filter can be used to pinpoint a wavelength (or range of wavelengths) of light to be emitted from optical fiber input 42, and is particularly useful with embodiments employing a non-coherent light source.

Referring to FIG. 7, a sensor 46 is optionally used to monitor the power of the beam as applied in the sample chamber 24. Sensor 46 is placed opposite optical fiber input 42 such that light passing through sample 26 strikes the sensor. The output from sensor 46 is routed to computer 206 for analysis and reporting. Sensor preferably comprises a photoelectric cell, such as a photodiode, phototransistor or the like. Sensor 46 enables the operator of the apparatus to confirm the accuracy of the power settings reported by light source 100 to computer 206.

Fluorescent radiation emitted from sample 26 is collected by optical fiber outputs 48, which are preferably mounted perpendicular to optical fiber input 42 to maximize the amount of fluorescent radiation (which is emitted at an angle perpendicular to the axis of incident exciting radiation from optical fiber input 42) collected from the sample. In the embodiment of FIGS. 7 and 8, two optical fiber outputs 48 are shown, but the invention encompasses the use of more or less of these outputs.

The radiation conveyed through optical fiber outputs 48 is filtered by output filters 50 to minimize the amount of extraneous light detected by the apparatus. Output filters 50 can be independently selected from the group consisting of narrow pass filters, low pass filters and high pass filters. For example, when YOYO-1 is used as the marking agent in the sample, output filters 50 can comprise a high pass filter that prevents the passage of light from sample chamber 24 having a wavelength less than about 500 nm. Since YOYO-1 has a maximum fluorescent intensity emission at about 536 nm, the high pass filter prevents excitation light (of about 488 nm) from erroneously inflating the detected amount of light emitted by YOYO-1. Of course, a narrow pass filter or a combination of a high pass filter and a low pass filter can be used to pinpoint a wavelength (or range of wavelengths) of light to be passed through optical fiber outputs 48.

The radiation collected by optical fiber outputs 48 is conveyed to detector 52, which reports to computer 206. Detector 52 preferably comprises a CCD.

Figure 9:
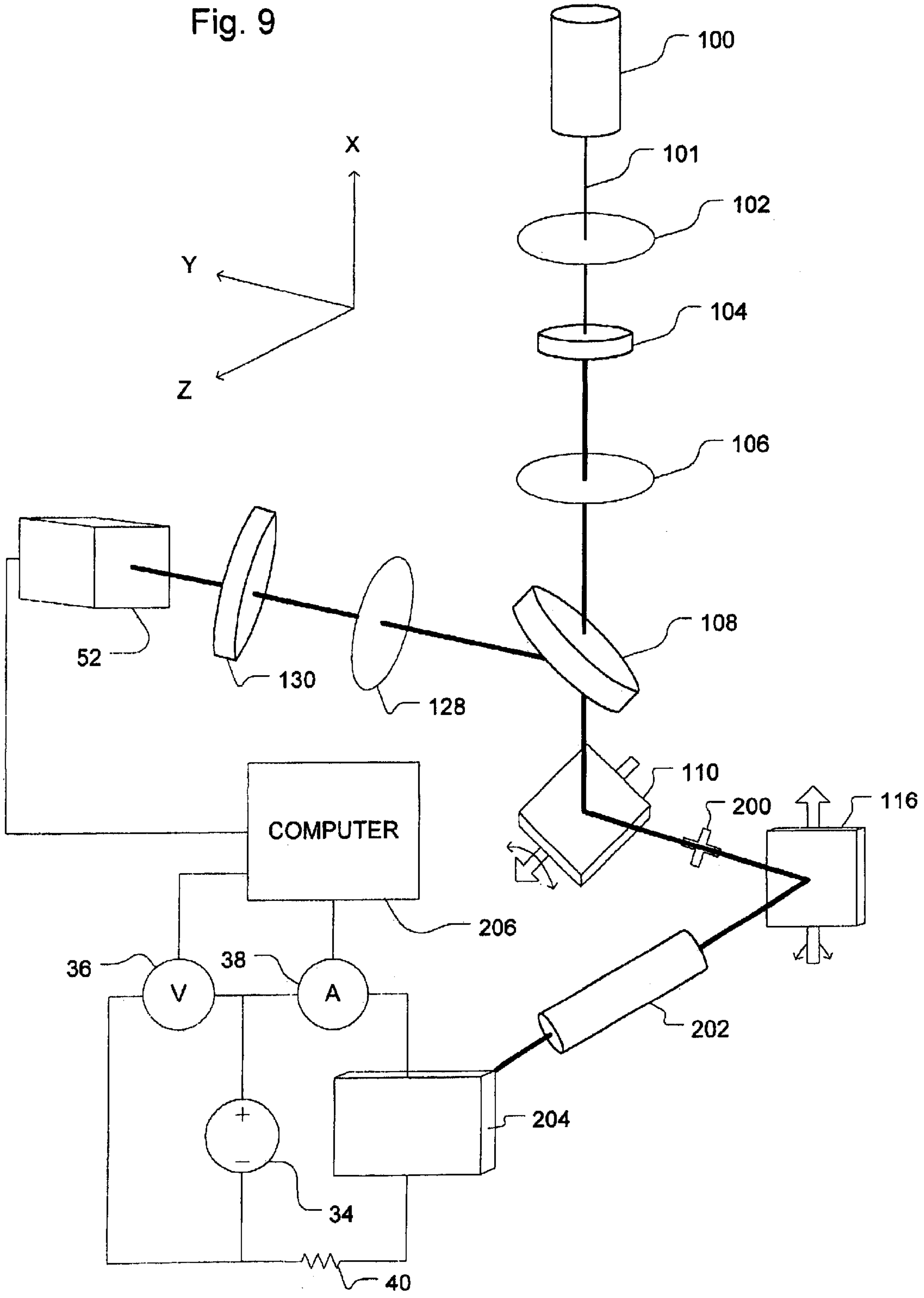
FIG. 9 is a schematic view of another embodiment of the apparatus of the invention.

FIG. 9 shows an alternative embodiment of the apparatus of the invention, which is particularly suitable for scanning an array of samples on a substrate. In FIG. 9, the incoming beam 101 from light source 100 passes through a spatial filter and beam expander (comprising lens 102, pinhole 104 and lens 106), and is expanded to match the diameter of the entrance pupil 200 of laser scan lens 202. The spatial filter and beam expander is optionally provided in front of light source 100 to improve the Gaussian profile of beam 101. Lens 102 and 106 can be, for example, 0.5 inch (1.27 cm) diameter 50 mm focal length anti-reflection coated piano convex glass lens or equivalent. Both lenses are preferably configured such that both their back focal planes coincide with pinhole 104. Pinhole 104 can have a wide range of aperture diameters, such as, e.g., 1–1000 $\mu$m, and preferably about 30 $\mu$m.

Scanning mirrors 110 and 116 deflect the beam in a raster scan, and rotate about axes that are perpendicular to each other and are placed close together, on either side of the entrance pupil of the laser scan lens. Laser scan lens 202 focuses the beam to a spot on sample array 204 (e.g., microtiter plate), and reflected light is collected by laser scan lens 202, descanned by scanning mirrors 116 and 110, and partially reflected by beam splitter 108 into a confocal detection arm comprised of lens 128, pinhole 130 and detector 52. In embodiments, pinhole 130 can be removed to provide a non-confocal imaging system. Light reflected back from the focused spot on the sample passes through pinhole 130 and is detected, but light from any other point in the sample runs into the edges of the pinhole and is not detected. The scan mirrors are computer-controlled to raster the focused spot across the sample.

Beamsplitter 108 is preferably a dichroic beamsplitter, which reflects the longer-wavelength fluorescence (or shorter-wavelength fluorescence in the case of up-converting labels, which emit radiation at shorter wavelengths than the excitation radiation—see, e.g., U.S. Pat. No. 5,674,698 to Zarling et al.) returning from the specimen into the confocal detection arm, while allowing reflected light, at the excitation wavelength, to pass through. In certain embodiments, beam splitter 108 can be, for example, a non-polarizing 50% beam splitter cube made by Melles Griot model number 03BSC007 or equivalent.

Computer 206 is connected to the detector 52 to receive, analyze, store and/or display a signal from the detector 52. Laser scan lenses are not usually used in imaging systems, and a beam of light will be collected by the lens that is wider than the incoming laser beam, but only the component of this beam that is parallel to and concentric with the incoming laser beam will pass through the pinhole and be detected. Thus, this is a true confocal imaging system, and will have optical image slicing properties similar to those of a confocal scanning laser microscope, except applied to much larger samples.

In certain embodiments, a stop with the same diameter as entrance pupil 200 of laser scan lens 202 can be placed at the entrance pupil position (just to the left of scanning mirror 116 in FIG. 9) if required, to reduce the out-of-focus part of the returning beam traveling back toward the confocal detector.

In certain embodiments wherein scanning mirror 116 has beam splitting properties, a detector is placed behind the mirror to detect non-confocal light. The beam splitting mirror is preferably dichroic and reflects light at the excitation wavelength returning from the specimen, while allowing the longer-wavelength fluorescence (or shorter-wavelength fluorescence in the case of up-converting labels) to pass through. Suitable dichroic mirrors include, e.g., a LWP-45°S-488R/520T-1025 made by CVI Laser Corp. or equivalent.

Alternatively, a beam splitter between sample array 204 and laser scan lens 202 can be used to divert a portion of light emitted from the sample array through a condenser lens to a detector. The beam splitter reflects the longer-wavelength fluorescence (or shorter-wavelength fluorescence in the case of up-converting labels) returning from the specimen into the condenser lens and detector, while allowing reflected light, at the excitation wavelength, to pass through.

Figure 10:
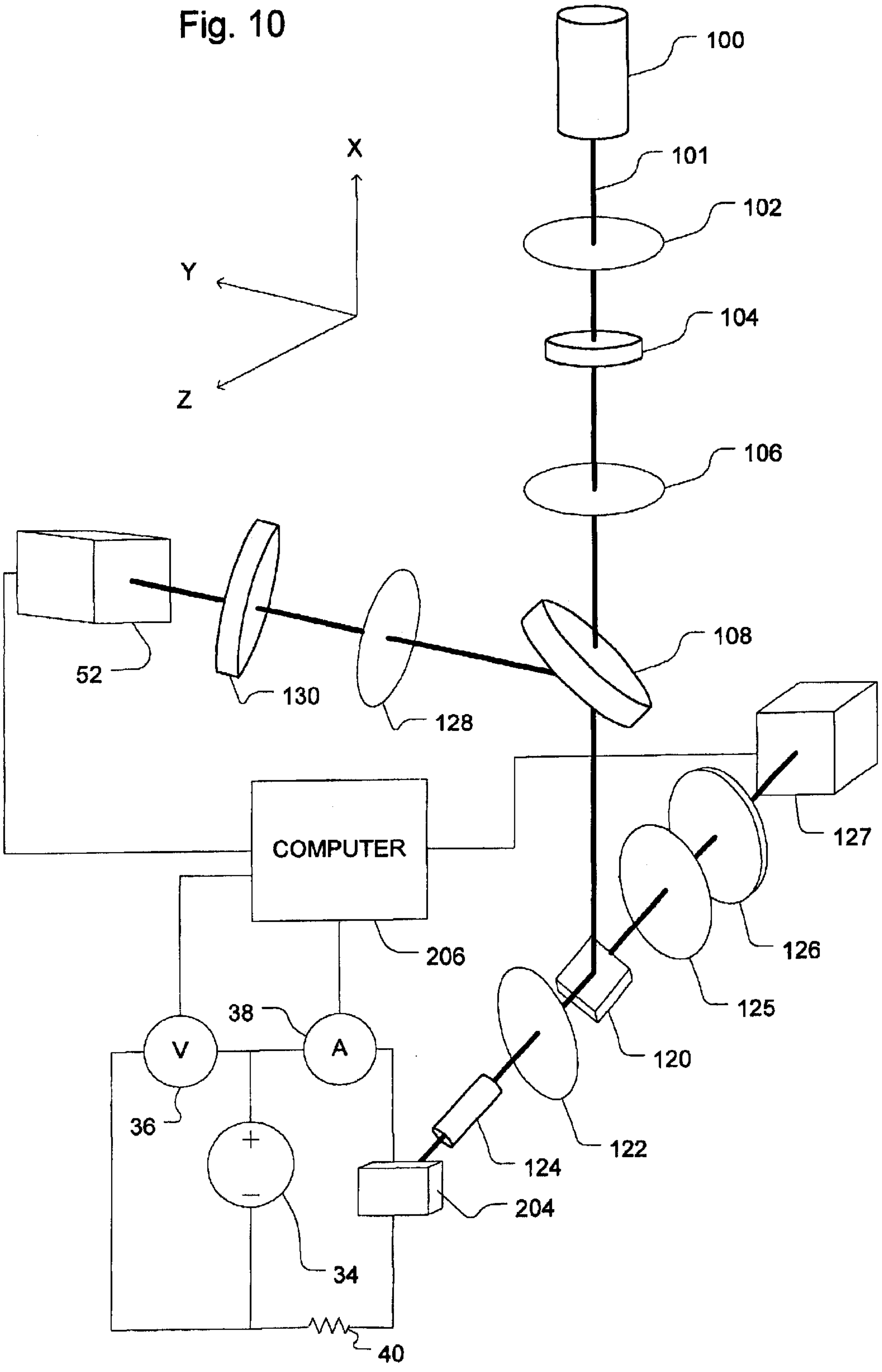
FIG. 10 is a schematic view of another embodiment of the apparatus of the invention.

FIG. 10 shows an alternative embodiment of the apparatus of the invention, which is particularly suitable for scanning an array of samples on a substrate.

Sample array 204 is preferably transparent to a wide spectrum of light. In some embodiments, sample array 204 is made of a conventional microscope glass slide or cover slip. It is preferable that the sample array be as thin as possible while still providing adequate physical support. Preferably, the sample array is less than about 1 mm thick, more preferably less than 0.5 mm thick. Typically, the sample array is a microscope glass slide of about 0.7 mm or 700 μm thick. In alternative embodiments, the sample array may be made of quartz or silica.

Sample array 204 can optionally be mounted on a flow cell as taught by U.S. Pat. No. 6,141,096 to Stern et al.

Light source 100 generates beam 101 to excite fluorescent targets in the flow cell. The laser is directed at sample array 204 through an optical train comprised of various optical elements which will be described below in detail to the extent that such elements differ from the embodiment of FIG. 9.

After passing through beam splitter 108, the excitation light is reflected by dichroic mirror 120. In certain embodiments, dichroic mirror 120 passes light having a wavelength greater than about 520 nm, but reflects light having a wavelength of about 488 nm. Consequently, the 488 nm light from the laser is reflected by dichroic mirror 120 toward optical lens 122. In certain embodiments, optical lens 122 is a 0.5 inch (1.27 cm) diameter—50 mm focal length anti-reflection coated plano-concave glass lens made by Newport or equivalent. The light then passes through a microscope objective 124 to sample array 204 for magnification of the sample image. Microscope objective 124, in some embodiments, may be a 10×0.3NA microscope objective, but other magnifications could also be used. In a preferred embodiment, the distance between lens 122 and microscope objective 124 is about 100 mm.

Microscope objective 124 focuses the light on samples in sample array 204. Preferably, the microscope objective produces a spot about 2 μm in diameter in its focal plane. The optical train described in the above embodiments produces a 2 μm diameter focal spot when used with a laser which generates a beam diameter of 1.4 mm, such as the Spectra-Physics model 2017.

In alternative embodiments, the 2 μm spot may be easily obtained when other types of light sources with different beam diameters are used. Since the diameter of the focal spot is inversely proportional to the diameter of the collimated beam produced by lens 106, the desired spot size may be achieved by varying the focal lengths of the spatial filter. Alternatively, a beam expander may be used to expand or compress the beam from the light source to obtain the desired spot size. For example, with a model 161C, which generates a beam diameter of 0.7 mm, a 2 μm diameter focal spot may be achieved if the ratio of the lens in the spatial filter is 1:2 instead of 1:1. Thus, by varying the focal lengths of the lenses in the spatial filter and/or using a beam expander, the appropriate excitation spot size may be achieved from various beam diameters.

In a preferred embodiment, the 2 μm spot has a power of 50 μW. Depending on the light source used, a variable neutral density filter can be inserted between the laser 100 and the optical train to attenuate the power of the laser to the desired power level.

Fluorescent emissions are collected by the microscope objective 124 and passed to optical lens 122. Optical lens 122 collimates the fluorescence and passes it to dichroic mirror 120. In practice, light collected by microscope objective contains both fluorescence emitted by the fluorescein and 488 nm laser light reflected from the sample array 204. The laser component reflected from the sample array is reflected by dichroic mirror 120 back to beam splitter 108. Beam splitter 108 directs the laser component through a lens 128. The lens, in some embodiments, can be 0.5 inch (1.27 cm) diameter—50 mm focal length anti-reflection coated plano convex glass lens made by Newport, but equivalent thereof may be used. Lens 128 focuses the laser component to detector 52. Preferably, a confocal pinhole 130 is located between lens 128 and detector 52. Pinhole 130 transmits substantially only the reflected light originating from the focal plane of the microscope to detector 52, while reflected light originating from out-of-focus planes are blocked. In certain embodiments, pinhole 171 has an aperture of about 50 $\mu$m.

Detector 52 can be, e.g., a photodiode that generates a voltage corresponding to the intensity of the detected light. The photodiode can be, e.g., a 13 DSI007 made by Melles Griot or equivalent, or other light detection devices, such as photomultiplier tube or avalanche photodiode may be used. Output from detector 52 is used by computer 206 to focus the laser at a point within a sample on sample array 204.

As for the fluorescent component emitted from sample array 204, most of it will pass through the dichroic mirror 120. The fluoresced light is then focused by a lens 125 to detector 127 (e.g., a photomultiplier tube) for detecting the number of photons present therein. Lens 125, in a preferred embodiment, is a 0.5 inch (1.27 cm) diameter—50 mm focal length anti-reflection coated piano convex glass lens made by Newport, but equivalent lens may be used. A pinhole 126 is preferably located between lens 125 and detector 127. Pinhole 126 transmits fluorescence originating from the focal plane and filters out light originating from other planes, such as from the glass or reagent. Accordingly, the signal-to-noise ratio of the fluoresced light is increased.

Additionally, a filter (not shown) is preferably located between detector 127 and pinhole 126 to filter out light having a wavelength other than the wavelength(s) of fluorescent emission. The filter further ensures that detector 127 detects substantially only fluoresced light.

In certain embodiments, detector 127 is a Hamamatsu R4457P photomultiplier tube with Hamamatsu C3866 preamplifier/discriminator. The photomultiplier tube generates approximately a 2 mV pulse for each photon detected. Each of these 2 mV pulses are converted to a TTL pulse by the preamplifier/discriminator. The TTL pulses, each one corresponding to a photon detected by the photomultiplier tube, are then collected by a data acquisition board, such as a National Instruments "Lab-PC+" or equivalent, which typically contains an Intel 8254 or equivalent counter/timer chip. The data represent the photon count as a function of sample array position.

After data are collected from a region (i.e., sample) of the sample array, sample array 204 is moved so that light can be directed at a different region on the sample array. Movement of sample array can be accomplished by a variety of means, including but not limited to, a conveyor belt, a rotating disk, an x-y-z table, or the like. The process is repeated until all samples on the sample array have been scanned. By counting the number of photons generated in a given area in response to the excitation light, it is possible to determine where fluorescently marked molecules are located on the sample array. Consequently, it is possible to determine which of the probes within a matrix of probes is complementary to a fluorescently marked target.

According to preferred embodiments, the intensity and duration of the light applied to the sample array is controlled by computer 206. By varying the laser power and scan stage rate, the signal-to-noise ratio may be improved by maximizing fluorescence emissions. As a result, the present invention can detect the presence or absence of a target on a probe as well as determine the relative binding affinity of probes and targets.

As in the embodiments depicted in FIGS. 7–9, an electric circuit comprising electrodes 32, voltage source 34, voltmeter 36, ammeter 38 and resistor 40, is provided in electrical communication with the samples.

The invention will be illustrated in more detail with reference to the following Examples, but it should be understood that the present invention is not deemed to be limited thereto.

EXAMPLES

Example 1

Sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. Equimolar amounts of complementary oligonucleotides were denatured at 95° C. for 10 min and allowed to anneal gradually as the temperature cooled to 21° C. over 1.5 hours. Double stranded DNA (dsDNA) oligonucleotides were dissolved in $ddH_2O$ at a concentration of 1 pmole/$\mu$l.

Sequence for the sense strand of the wild-type target DNA (SEQ ID NO:1): 5'-TGG CAC CAT TAA AGA AAA TAT CAT CTT

TGG TGT TTC CTA TGA TGA ATA TA-3'.

Sequence for the antisense strand of the wild-type target DNA (SEQ ID NO:1): 5'-TAT ATT CAT CAT AGG AAA CAC CAA

AGA TGA TAT TTT CTT TAA TGG TGC CA-3'.

The predicted melting temperature ($T_m$) of dsDNA (SEQ ID NO:1) is 65.2° C.

SEQ ID NO:2 was a 50-mer mutant dsDNA target sequence identical to wild-type target DNA (SEQ ID NO:1) except for a one base pair mutation (underlined) at amino acid position 507 at which the wild-type sequence CAT was changed to C<u>G</u>T.

Sequence for the sense strand of SEQ ID NO:2: 5'-TGG CAC CAT TAA AGA AAA TAT C<u>G</u>T CTT TGG TGT TTC CTA TGA TGA ATA TA-3'.

Sequence for the antisense strand of SEQ ID NO:2: 5'-TAT ATT CAT CAT AGG AAA CAC CAA AGA <u>C</u>GA TAT TTT CTT TAA TGG TGC CA-3'.

The predicted melting temperature ($T_m$) of dsDNA (SEQ ID NO:2) is 66.0° C.

SEQ ID NO:3 was a 50-mer mutant dsDNA target sequence identical to wild-type target DNA (SEQ ID NO:1) except for a consecutive two base pair mutation (underlined) at amino acid positions 506 and 507 at which the wild-type sequence CAT was changed to <u>AC</u>T.

Sequence for the sense strand of SEQ ID NO:3: 5'-TGG CAC CAT TAA AGA AAA TAT <u>AC</u>T CTT TGG TGT TTC CTA TGA TGA ATA TA-3'.

Sequence for the antisense strand of SEQ ID NO:3: 5'-TAT ATT CAT CAT AGG AAA CAC CAA AGA <u>GT</u>A TAT TTT CTT TAA TGG TGC CA-3'.

The predicted melting temperature ($T_m$) of dsDNA (SEQ ID NO:3) is 65.2° C.

The PNA probes used in the Examples were synthesized, HPLC purified and confirmed by mass spectroscopy by Commonwealth Biotechnologies, Inc. (Richmond, Va., USA). PNA probes were first dissolved in 0.1% TFA (trifluoroacetic acid) to a concentration of 10 mg/ml, and then diluted to 1 mg/ml by the addition of $ddH_2O$. Final PNA stock solutions were prepared in $ddH_2O$ at a concentration of 1 pmole/μl.

Probe No. 1 was a 15-mer antiparallel PNA probe designed to be completely complementary to a 15 nucleotide segment of the sense strand of the 50-mer wild-type target DNA (SEQ ID NO:1), overlapping amino acid positions 505 to 510 (Nature 380, 207 (1996)). The probe had the following structure (SEQ ID NO:8):

5'-H-CAC CAA AGA TGA TAT-Lys-$CONH_2$-3'

The hybridization reaction mixture (80 μl) contained the following: 2 pmoles of target dsDNA, 2 pmoles of PNA probe, 0.5×TBE and 250 nM of the DNA intercalator YOYO-1 (Molecular Probes, Eugene, OR, USA). Samples were placed into a 3 mm quartz cuvette and were subjected to 1 or 5 volts DC (V) electrification for 15 seconds. The amperometric assay consisted of the monitoring of current while the voltage was being applied to the solution. A temperature probe was placed in each solution to measure temperature at the time of amperometric assessment. At 1 volt, a current peak was observed during the first 2 seconds of electrification. The current declined sharply over the following 13 seconds. Experiments applying 5 volts gave rise to currents that remained relatively stable over the entire electrification period (15 seconds).

A series of experiments were carried out where the conductance values were observed when no DNA or PNA was present (control), or when wild-type SEQ ID NO:1, mutant SEQ ID NO:2 or mutant SEQ ID NO:3 were reacted with antiparallel PNA Probe No. 1. FIGS. 1A and 1B plot the data obtained for conductance in the individual experiments. FIG. 1A displays the results of the application of 1V electrification and FIG. 1B the application of 5V. Double stranded DNA:PNA hybrid triplexes consisting of perfectly complementary sequences (SEQ ID NO:1+Probe No. 1) allowed maximum intercalation of YOYO-1, yielding the highest conductance values (depicted on the figures as negative current values) throughout the entire 15 seconds of 1V application. The normalized peak conductance for the triplex hybridization of the antiparallel PNA probe with a 1 bp mismatched dsDNA (SEQ ID NO:2+Probe No. 1) and with the 2 bp mismatched dsDNA (SEQ ID NO:3+Probe No. 1) were respectively 79% and 96% lower than that observed with the perfectly matched dsDNA:PNA triplex hybrid (SEQ ID NO:1+Probe No. 1) during the first second of voltage application (FIG. 1A). Similar percent decreases in conductance between perfectly complementary triplexes and triplexes containing base pair mismatches were obtained when the conductance values over the entire 15 seconds of voltage application were averaged. In FIG. 1A the 1 bp and 2 bp mismatched dsDNA:PNA hybrids resulted in average conductance values that were 65% and 91% lower, respectively, than those for the perfectly matched dsDNA:PNA hybrid. All experiments expressed in FIG. 1A were carried out at room temperature (23° C.). As the degree of mismatch between the probe and the double stranded target increased, the level of intercalation by YOYO-1 diminished and the level of conductance decreased. These relationships were also observed when the experiments referred to above were repeated and a higher voltage (5V) was applied. During the 5V application the normalized average conductance values for the 1 bp mismatched dsDNA:PNA triplex (SEQ ID NO:2+Probe No. 1) and the 2 bp mismatched dsDNA:PNA triplex (SEQ ID NO:3+Probe No. 1) were respectively 52% and 67% lower than that observed for the perfectly matched dsDNA:PNA triplex (SEQ ID NO:3+Probe No. 1) (FIG. 1B). Experiments expressed in FIG. 1B were performed at room temperature (23° C.).

When the experiments were repeated with the temperature increased to 50° C. and 65° C., similar amperometric values were observed. At 50° C., the application of 1V for 15 seconds to the perfectly matched dsDNA:PNA triplex (SEQ ID NO:1+Probe No. 1) produced an average current of −0.25 μAmp as compared to values of −0.15 μAmp (a 40% reduction) and −0.06 μAmp (a 76% reduction) for the 1 bp mismatched dsDNA:PNA triplex (SEQ ID NO:2+Probe No. 1) and the 2 bp mismatched dsDNA:PNA triplex (SEQ ID NO:3+Probe No. 1), respectively (FIG. 1C). At 65° C., similar observations were noted when 1V of electricity was applied for 15 seconds. Perfectly matched nucleic acid hybrids produced an average current of −0.37 μAmp compared with −0.16 μAmp (a 57% reduction) and −0.01 μAmp (a 97% reduction) for 1 bp and 2 bp mismatched hybrids, respectively (FIG. 1C). The application of 5 volts at high temperatures produced analogous results. While experiments performed at 50° C. generated average currents of −0.27 μAmp, −0.13 μAmp (a 52% reduction), and −0.08 μAmp (a 70% reduction), for perfectly matched hybrids, 1 bp mismatched hybrids, and 2 bp mismatched hybrids, respectively, experiments performed at 65° C. resulted in average current values of −0.31 μAmp, −0.14 μAmp (a 55% reduction), and −0.10 μAmp (a 68% reduction) for the same three respective groups (FIG. 1D). For all of the foregoing experiments, dsDNA was not denatured prior to triplex hybridization with the antiparallel PNA Probe No. 1.

Similar experiments were done at varying temperatures after the hybridization mixes had been heated to 65° C. and immediately allowed to cool. After cooling to room temperature (23° C.), applying 1V for 15 seconds to the perfectly matched sample (SEQ ID NO:1+Probe No. 1) produced an average current of −0.18 μAmp. By comparison, values of −0.06 μAmp (a 67% reduction) and −0.05 μAmp (a 72% reduction) for the 1 bp mismatched dsDNA:PNA triplex hybrid (SEQ ID NO:2+Probe No. 1) and the 2 bp mismatched dsDNA:PNA triplex hybrid (SEQ ID NO:3+Probe No. 1), were respectively observed (data not shown). When the samples were cooled from 65° C. to 50° C., similar observations were noted when 1V was subsequently applied for 15 seconds. The perfectly matched sample (SEQ ID NO:1+Probe No. 1) produced an average current of −0.23 μAmp compared with −0.11 μAmp (a 52% reduction) and −0.01 μAmp (a 96% reduction) observed for the 1 bp and 2 bp mismatched samples, respectively (data not shown). When 5V was applied after cooling to 23° C. or 50° C., the average current generated in the perfectly matched triplex hybrid (SEQ ID NO:1 +Probe No. 1), the 1 bp mismatched triplex hybrid (SEQ ID NO:2+Probe No. 1), and the 2 bp mismatched triplex hybrid (SEQ ID NO:3+Probe No. 1) were: −0.15 μAmp, −0.09 μAmp (a 40% reduction), and −0.07 μAmp (a 53% reduction), respectively at 23° C., and −0.23 μAmp, −0.09 μAmp (a 61% reduction), and −0.09 μAmp (a 61% reduction), respectively at 50° C. (data not shown).

Pretreatment of hybridization mixes at 65° C. (the $T_m$ of the 50-mer dsDNA sequences) followed by cooling did not significantly affect the difference in conductance observed between perfectly complementary dsDNA:PNA triplexes and those containing 1 or 2 bp mismatches when measured directly at 23° C. or 50° C. (without preheating at 65° C.) when an antiparallel PNA probe was used. Clearly, the antiparallel PNA probe in the presence of the DNA intercalator YOYO-1 was able to form triplex structures with the dsDNA targets. Application of low levels of electricity (such as 1V or 5V) allowed the perfectly matched dsDNA:PNA triplex sequences to be distinguished from those containing 1 bp or 2 bp mutations, without prior denaturation of sequences.

Example 2

FIG. 2 demonstrates that the amperometric assay of the invention can also discriminate between perfectly matched dsDNA:PNA triplex hybrids and those containing 1 bp or 2 bp mismatches when the PNA probe used is in a parallel orientation with respect to the target DNA sequence. Probe No. 2 was a 15-mer PNA probe identical in sequence to Probe No. 1, but was synthesized to match the parallel orientation of the target DNA, instead of the conventional anti-parallel orientation. Probe No. 2 had the following structure (SEQ ID NO:9):

5'-H-TAT AGT AGA AAC CAC-Lys-$CONH_2$-3'

Experiments with assay conditions identical to those described in Example 1 were carried out with the sole difference that Probe No. 2 was used in place of Probe No. 1. When 1 volt was applied, the average current for a 1 bp mismatched dsDNA:PNA triplex (SEQ ID NO:2+Probe No. 2), and a consecutive 2 bp mismatched dsDNA:PNA triplex (SEQ ID NO:3+Probe No. 2), were respectively 25% and 32% lower at 23° C., respectively 30% and 23% lower at 50° C., and respectively 28% and 53% lower at 65° C. than that observed with the perfectly matched dsDNA:PNA triplex (SEQ ID NO:1+Probe No. 2) at matching temperatures (FIG. 2A).

Similar results were obtained when 5V (instead of 1V) was applied for 15 seconds. Perfectly matched dsDNA:PNA hybrids at 23° C., 50° C. and 65° C. generated average currents of −0.15 mAmp, −0.24 mAmp and −0.17 mAmp, respectively (FIG. 2B). Incompletely complementary triplexes with a 1 bp mismatch and a 2 bp mismatch produced average currents that were 27% less (−0.11 mAmp) and 53% less (−0.07 mAmp), respectively at 23° C., 21% less (−0.19 mAmp) and 46% less (−0.13 mAmp), respectively at 50° C., and unchanged (−0.17 mAmp) and 18% less (−0.14 mAmp), respectively at 65° C., than that achieved by the perfectly matched hybrid samples (FIG. 2B).

The results illustrated in FIGS. 2A and 2B indicated that when the parallel PNA Probe No. 2 was used, the differences in conductivity obtained between perfectly matched dsDNA:PNA triplexes and those containing 1 bp or 2 bp mismatches were less dramatic than that achieved with the antiparallel PNA Probe No. 1 (FIG. 1).

However, experiments involving parallel Probe No. 2 and the application of 5V after the samples have been heated to 65° C. and immediately allowed to cool disclosed amperometric measurements which demonstrated enhanced signaling differences between perfectly matched dsDNA:PNA triplexes and the 1 bp or 2 bp mismatched dsDNA:PNA triplexes (FIG. 2C). The perfectly matched hybrids (SEQ ID NO:1+Probe No. 2), the 1 bp mismatched hybrids (SEQ ID NO:2+Probe No. 2) and the 2 bp mismatched hybrids (SEQ ID NO:3+Probe No. 2) yielded average conductance values of −0.19 mAmps, −0.08 mAmps and −0.06 mAmps, respectively at 23° C., −0.17 mAmps, −0.09 mAmps and −0.07 mAmps, respectively at 50° C., and −0.23 mAmps, −0.13 mAmps and −0.08 mAmps, respectively at 65° C. This translated to reductions in conductivity of 58% and 68% at 23° C., 47% and 59% at 50° C., and 43% and 65% at 65° C. for the 1 bp and 2 bp mismatched samples, respectively, when compared to the values achieved by the perfectly complementary samples (FIG. 2C).

Therefore, both antiparallel and parallel PNA probes in the amperometric assay are capable of discriminating between perfectly complementary dsDNA targets and incompletely complementary dsDNA targets containing 1 bp or 2 bp mutations.

Example 3

Probe No. 3 was a 15-mer ssDNA probe identical in sequence and orientation to the 15-mer antiparallel PNA Probe No. 1 (SEQ ID NO:8). Probe No. 3 had the following structure:

5'-CAC CAA AGA TGA TAT-3'

The specificity of the amperometric assay was further investigated by reacting ssDNA Probe No. 3 with the 50-mer wild-type and mutant dsDNA target sequences in the absence of prior denaturation. The assay conditions were identical to that described in Example 1.

Enhanced by the DNA intercalator YOYO-1, dsDNA:ssDNA triplexes were formed between 30° C. and 65° C. Upon 1 volt treatment, the perfectly matched DNA triplex, consisting of SEQ ID NO:1+Probe No. 3, yielded the highest conductivity values (FIG. 3A). In contrast, incompletely complementary probe and target combinations generating a 1 bp mismatch (SEQ ID NO:2+Probe No. 3), and a consecutive 2 bp mismatch (SEQ ID NO:3+Probe No. 3), resulted in average conductance values that were 14% and 64% lower at 23° C., 30% and 70% lower at 50° C., and 25% and 72% lower at 65° C., respectively, than that observed with the perfectly complementary sequences at matching temperatures (FIG. 3A). The application of a higher voltage (5V) to these samples resulted in greater amperometric differences observed between perfectly matched and mismatched samples, than that obtained at 1V, particularly at lower temperatures. After a 5V treatment for 15 seconds, the average currents for the 1 bp mismatched DNA triplex and the 2 bp mismatched DNA triplex were 54% and 78% lower, respectively at 23° C., 68% and 70% lower, respectively at 50° C., and 33% and 61% lower, respectively at 65° C., than that observed with the perfectly matched DNA triplex at matching temperatures (FIG. 3B).

In similar electricity experiments, the hybridization mixes were heated to 65° C. and were either maintained at this temperature or immediately allowed to cool to 50° C. or 23° C. prior to application of 1V or 5V. A 1V treatment for 15 seconds to the perfectly matched DNA triplex sequences (SEQ ID NO:1+Probe No. 3) produced the highest conductance values at 23° C., 50° C. and 65° C. (FIG. 3A). The DNA triplexes containing a 1 bp mismatch (SEQ ID NO:2+Probe No. 3) or a 2 bp mismatch (SEQ ID NO:3+Probe No. 3) were less conductive by 21% and 63%, respectively at 23° C., by 18% and 74%, respectively at 50° C., and by 12% and 106%, respectively at 65° C. (FIG. 3A). Similarly, when 5V were applied for 15 seconds to pre-heated samples, the average conductance values for the 1 bp mismatched DNA triplexes and the 2 bp mismatched DNA triplexes were reduced by 24% and 104%, respectively at 23° C., by 42% and 44%, respectively at 50° C., and by 38% and 102%, respectively at 65° C., when compared to the average conductance values generated by the perfectly matched DNA triplexes (FIG. 3B).

The observation that the antiparallel PNA probe (FIG. 1) and ssDNA probe (FIG. 3) behaved in a similar fashion in the amperometric assay, suggested that the backbone of the nucleic acid entity used as the probe was not particularly important.

The presence of YOYO-1 allowed the dsDNA targets and the ssDNA probe to form a triple helix conformation capable of generating different electrical charges depending on the level of sequence complementarity between the target and the probe in solution. As the degree of mismatch between the probe and the target increased, the level of conductance decreased, proving the reliability of the amperometric assay when a natural DNA probe was used in the absence of prior denaturation.

Example 4

In the amperometric assays illustrated in Examples 1 to 3, the DNA intercalator YOYO-1 was added to the solution containing the hybridization mixes. Intercalation by YOYO-1 facilitated the formation of the dsDNA:PNA triplexes and dsDNA:ssDNA triplexes. The possibility of utilizing an intercalator moiety covalently tethered to a ssDNA probe in the amperometric assay was evaluated in Example 4.

Acridine is an alternative dsDNA intercalator, that also possesses the ability to intercalate into triplex nucleic acid structures, thereby stabilizing the triple helix formation.

See, e.g., Kukreti et al., "Extension of the range of DNA sequences available for triple helix formation: stabilization of mismatched triplexes by acridine-containing oligonucleotides." 25 Nucleic Acids Research 4264–4270 (1997). A ssDNA probe containing an acridine molecule (Glen Research, Sterling, VA, USA) covalently attached at the 3' end was synthesized on a DNA synthesizer (Expedite 8909, PerSeptive Biosystems) and purified by HPLC.

Probe No. 4 was a 15-mer ssDNA probe identical in sequence and orientation to the 15-mer Probe No. 3 (and thus also identical in sequence and orientation to the 15-mer antiparallel PNA Probe No. 1 (SEQ ID NO:8)) but with the addition of an acridine moiety at the 3' position. The probe had the following structure:

5'-CAC CAA AGA TGA TAT-acridine-3'

The hybridization reaction mixture (80 $\mu$l) contained the following: 2 pmoles of target dsDNA, 2 pmoles of ssDNA Probe No. 4 and 0.5×TBE. Samples were placed into a 3 mm quartz cuvette and were subjected to 5V DC electrification for 11 seconds at 23° C. The current and temperature were monitored as described in Example 1.

As shown in FIG. 4, the ssDNA Probe No. 4 was able to hybridize with the 50-mer perfectly matched dsDNA target (SEQ ID NO:1) as a result of the stable intercalation of the covalently tethered acridine moiety, generating an average current of −0.53 mAmp. By comparison, the less stable DNA triplexes containing a 1 bp mismatch (SEQ ID NO:2+Probe No. 4) or a 2 bp mismatch (SEQ ID NO:3+Probe No. 4) produced average currents that were 52% and 66% lower, respectively, than that achieved by the perfectly matched DNA triplex, when normalized against the control (Probe No. 4 without target DNA) (FIG. 4).

Therefore, the acridine attached to a ssDNA probe was equally as efficient as untethered YOYO-1 in forming triple DNA helices that generated different electrical currents depending on the level of sequence complementarity between the target and the probe in the amperometric assay.

Example 5

Sense and antisense 15-mer ssDNA target sequences, derived from exon 10 of the human cystic fibrosis gene, were synthesized, purified and annealed as described in Example 1. DsDNA oligonucleotides were dissolved in $ddH_2O$ at a concentration of 1 pmole/$\mu$l.

SEQ ID NO:4 was a 15-mer dsDNA target sequence derived from SEQ ID NO:1, designed to be completely complementary to Probe No. 1.

Sequence for the sense strand of the wild-type target DNA (SEQ ID NO:4): 5'-ATA TCA TCT TTG GTG-3'.

Sequence for the antisense strand of the wild-type target DNA (SEQ ID NO:4): 5'-CAC CAA AGA TGA TAT-3'.

The predicted melting temperature ($T_m$) of dsDNA (SEQ ID NO:4) is 40.0° C.

SEQ ID NO:5 was a 15-mer mutant dsDNA target sequence identical to wild-type target DNA (SEQ ID NO:4) except for a one base pair mutation (underlined), at which the sequence TTT was changed to TAT.

Sequence for the sense strand of the mutant target DNA (SEQ ID NO:5):

5'-ATA TCA TCT ATG GTG-3'.

Sequence for the antisense strand of the mutant target DNA (SEQ ID NO:5):

5'-CAC CAT AGA TGA TAT-3'.

The predicted melting temperature ($T_m$) of dsDNA (SEQ ID NO:5) is 40.0° C.

SEQ ID NO:6 was a 15-mer mutant dsDNA target sequence identical to wild-type target DNA (SEQ ID NO:4) except for a consecutive two base pair mutation (underlined), at which the sequence ATC was changed to GGC.

Sequence for the sense strand of the mutant target DNA (SEQ ID NO:6):

5'-ATA TCG GCT TTG GTG-3'.

Sequence for the antisense strand of the mutant target DNA (SEQ ID NO:6):

5'-CAC CAA AGC CGA TAT-3'.

The predicted melting temperature ($T_m$) of dsDNA (SEQ ID NO:6) is 44.0° C.

SEQ ID NO:7 was a 15-mer mutant dsDNA target sequence identical to wild-type target DNA (SEQ ID NO:4) except for a separated three base pair mutation (underlined), wherein three 1 bp mutations were separated by 3 base pairs each. The sequences ATC, TCT and TGG were changed to ACC, TAT and TAG, respectively.

Sequence for the sense strand of the mutant target DNA (SEQ ID NO:7): 5'-ATA CCA TAT TTA GTG-3'.

Sequence for the antisense strand of the mutant target DNA (SEQ ID NO:7): 5'-CAC TAA ATA TGG TAT-3'.

The predicted melting temperature ($T_m$) of dsDNA (SEQ ID NO:7) is 38.0° C.

The hybridization reaction mixture (80 $\mu$l) contained the following: 2 pmoles of target dsDNA, 2 pmoles of parallel PNA Probe No. 2, 0.5×TBE and 250 nM of the DNA intercalator YOYO-1. The reaction mixtures were incubated at 95° C. for 5–10 minutes to allow denaturation, and then maintained at 65° C. until assayed. Samples were placed into a quartz cuvette, irradiated with an argon ion laser beam having a wavelength of 488 nm and monitored for fluorescent emission at 65° C. Concurrent temperature measurements were achieved by a software-controlled temperature probe placed directly into each sample. The maximum fluorescent intensity occurred at a wavelength of 536 nm, indicative of intercalation of YOYO-1 in the PNA:DNA hybrids. As a second assay, following the initial laser irradiation of each sample, the same samples were subjected to 1V DC electrification for 4 seconds. During the final second of electrification the samples were irradiated a second time with the argon ion laser and monitored for fluorescent emission at 65° C. Fluorescent intensities were plotted as a function of wavelength for each sample analyzed.

SsDNA:PNA hybrids consisting of perfectly complementary sequences (SEQ ID NO:4+Probe No. 2) allowed maximum intercalation of YOYO-1, yielding the highest fluorescent intensities (FIG. 5A). The fluorescent intensities for a 1 bp mismatched ssDNA:PNA hybrid (SEQ ID NO:5+Probe No. 2), a consecutive 2 bp mismatched ssDNA:PNA hybrid (SEQ ID NO:6+Probe No. 2), and a separated 3 bp mismatched ssDNA:PNA hybrid (SEQ ID NO:7+Probe No. 2) were all lower than that observed with the perfectly matched ssDNA:PNA hybrid at 65° C. (FIG. 5 and data not shown). As the degree of mismatch between the probe and the target increased, the level of intercalation by YOYO-1 diminished and hence the level of fluorescent intensity decreased. Only background levels of fluorescence were observed when no DNA or PNA was present (YOYO-1 alone) (FIG. 5A).

When the perfectly matched ssDNA:PNA hybrids were subjected to 1V of electricity for 4 seconds at 65° C., the fluorescent intensity remained relatively constant, decreasing by only 2% (FIG. 5A). In contrast, application of 1V to the incompletely complementary duplexes containing a 1 bp mismatch (FIG. 5B), a 2 bp mismatch (FIG. 5C) and a 3 bp mismatch (data not shown) produced fluorescent intensities that were 18%, 39% and 71% lower, respectively, than that achieved with the same samples irradiated in the absence of electricity. Treatment with low levels of electricity (such as 1V) further diminished the stability of the ssDNA:PNA hybrids containing bp mismatches. As the degree of sequence complementarity between the probe and the target decreased, the level of fluorescent intensity diminished dramatically in the presence of electricity, providing a highly reliable and accurate second assay to differentiate between perfectly matched sequences and those containing 1 bp, 2 bp or 3 bp mutations.

Example 6

The hybridization assay in Example 5 was performed after denaturation of the dsDNA target sequences and measured ssDNA:PNA hybrid formation at a temperature above the melting point ($T_m$) of the dsDNA targets. Example 6 will demonstrate the reliability of the fluorescent intensity assay in the absence and presence of applied electricity to differentiate between perfect matches and base pair mismatches without the requirement for prior denaturation.

The hybridization reaction mixture (80 μl) contained the following: 4 pmoles of target dsDNA, 4 pmoles of antiparallel PNA Probe No. 1, 0.5×TBE and 250 nM of the DNA intercalator YOYO-1. Samples were placed into a quartz cuvette, irradiated with an argon ion laser beam having a wavelength of 488 nm for 80 msec and monitored for fluorescent emission at 23° C. Concurrent temperature measurements were achieved by a software-controlled temperature probe placed directly into each sample. The maximum fluorescent intensity occurred at a wavelength of 536 nm, indicative of intercalation of YOYO-1 in the PNA:DNA hybrids. As a second assay, following the initial laser irradiation of each sample, the same samples were subjected to 20V DC electrification for 4 seconds. Immediately after 3 seconds of electrification the samples were irradiated a second time with the argon ion laser for 80 msec and monitored for fluorescent emission at 23° C. Fluorescent intensities were plotted as a function of wavelength for each sample analyzed.

Enhanced by the intercalator YOYO-1, dsDNA:PNA triplexes were formed at 23° C. The highest fluorescent intensity was achieved when the wild-type 50-mer dsDNA target sequence (SEQ ID NO:1) was hybridized with the 15-mer antiparallel PNA Probe No. 1 (FIG. 6). By comparison, the fluorescent intensities for a 1 bp mismatched dsDNA:PNA triplex (SEQ ID NO:2+Probe No. 1) and a consecutive 2 bp mismatched dsDNA:PNA triplex (SEQ ID NO:3+Probe No. 1) were 60% and 91% lower, respectively, than that observed with the perfectly matched dsDNA:PNA triplex at 23° C. (FIG. 6). When no DNA or PNA was present in the reaction mixture containing YOYO-1, only background levels of fluorescence were observed.

The difference in fluorescent intensities obtained by the perfectly complementary triplexes and those containing 1 bp or 2 bp mismatches were significantly greater than that achieved between perfectly matched duplexes and incompletely complementary duplexes (compare FIGS. 5 and 6). Clearly the fluorescent intensity assay of triplex formation possessed enhanced discriminatory ability to detect base pair mismatches.

Moreover, even further discrimination between wild-type and mutated sequences was possible with the secondary application of electricity. A 20V treatment for 3 seconds to the perfectly matched dsDNA:PNA triplexes produced a fluorescent intensity spectrum virtually identical to that achieved by the same sample not subjected to electricity (FIG. 6). However, application of 20V for 3 seconds to the incompletely complementary triplexes containing a 1 bp mismatch and a 2 bp mismatch produced fluorescent intensities that were 23% and 71% lower, respectively, than that obtained with the same samples irradiated in the absence of electricity (FIG. 6). The 20V treatment of electricity did not affect the stability of the perfectly complementary triplexes, but weakened the stability of the dsDNA:PNA triplexes containing base pair mismatches at a level dependent on the degree of sequence complementarity between the probe and the target. Therefore, the application of electricity to the fluorescent intensity assay provided an even more highly reliable assay to distinguish between wild-type sequences and those containing 1 bp or 2 bp mutations, without prior denaturation of sequences.

While the invention has been described in detail and with reference to specific examples thereof, it will be apparent to one skilled in the art that various changes and modifications can be made without departing from the spirit and scope thereof.

What is claimed is:

1. An apparatus for assaying specific binding of a probe to a target, said apparatus comprising:

a sample support for supporting a sample containing the probe and the target;

a light source for irradiating the sample;

an optical train for conveying light from the light source to the sample;

a light detector for detecting light emitted from the sample;

an electricity source for providing an electric charge through the sample;

an electrical property detector for detecting an electrical property of the sample; and a data analysis device in communication with the light detector and the electrical property detector, wherein the data analysis device is adapted to:

(a) (1) produce an optical determination of probe-target binding as a function of light emitted from the sample, (2) produce an electrical determination of probe-target binding as a function of the electrical property, and (3) compare the optical determination with the electrical determination to assay specific binding of the probe to the target; or (b) (1) produce a pre-electrification determination of probe-target binding as a function of light emitted from the sample prior to providing the electric charge through the sample, (2) produce a post-electrification determination of probe-target binding as a function of light emitted from the sample concurrent with and/or subsequent to providing the electric charge through the sample, and (3) compare the pre-electrification determination with the post-electrification determination to assay specific binding of the probe to the target.

2. The apparatus of claim 1, adapted to assay specific binding between the target, comprising a nucleic acid sequence, and the probe, comprising a nucleic acid sequence or a nucleic acid analog sequence.

3. The apparatus of claim 1, adapted to assay specific binding between the target, comprising an amino acid sequence, and the probe, comprising an amino acid sequence or an amino acid analog sequence.

4. The apparatus of claim 1, wherein the sample support contains a single sample or an array of samples.

5. The apparatus of claim 1, wherein the light source is a laser.

6. The apparatus of claim 1, wherein the optical train comprises optical fibers and filters.

7. The apparatus of claim 1, wherein the optical train comprises lenses, mirrors, beam splitters and filters.

8. The apparatus of claim 7, wherein the optical train conveys light from the sample to the light detector.

9. The apparatus of claim 8, wherein the light conveyed from the sample to the light detector is confocal.

10. The apparatus of claim 9, wherein a portion of the light from the sample is conveyed to a second light detector as non-confocal light.

11. The apparatus of claim 1, wherein the light detector comprises a photoelectric cell.

12. The apparatus of claim 1, wherein the electricity source is a direct current voltage outlet, generator or battery.

13. The apparatus of claim 1, wherein the electricity source is adapted to provide a voltage of about 1 V to 27 V through the sample.

14. The apparatus of claim 1, wherein the electrical property detector comprises at least one of a voltmeter and an ammeter.

15. The apparatus of claim 1, wherein the electrical property detector is adapted to measure conductance of the sample.

16. The apparatus of claim 1, wherein the data analysis device is adapted to produce the optical determination of probe-target binding by comparing an intensity of the light emitted by the sample with a reference intensity for a reference sample.

17. The apparatus of claim 1, wherein the data analysis device is adapted to produce the electrical determination of probe-target binding by comparing a conductance of the sample with a reference conductance for a reference sample.

18. The apparatus of claim 1, wherein the data analysis device is adapted to compare a pre-electrification intensity of light emitted by the sample with a post-electrification intensity of light emitted by the sample.

19. The apparatus of claim 1, wherein the sample support comprises an impermeable surface, a semipermeable surface, a biochip, a solid substrate, a microwell or a microchannel.

* * * * *

SEQUENCE LISTING

<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 1
tggcaccatt aaagaaaata tcatctttgg tgtttcctat gatgaatata 50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 2
tggcaccatt aaagaaaata tcgtctttgg tgtttcctat gatgaatata 50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 3
tggcaccatt aaagaaaata tactctttgg tgtttcctat gatgaatata 50

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 4
atatcatctt tggtg 15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 5
atatcatcta tggtg 15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: derived from exon 10 of the human cystic fibrosis gene

<400> SEQUENCE: 6

-continued

```
atatcggctt tggtg                                                   15


<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 7

ataccatatt tagtg                                                   15


<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: ssDNA probe
      wherein the 3' end of each base is covalently bonded
      to a lysine N-terminal leaving a free carboxyl group

<400> SEQUENCE: 8

caccaaagat gatat                                                   15


<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: ssDNA probe
      wherein the 3' end of each base is covalently bonded
      to a lysine N-terminal leaving a free carboxyl group

<400> SEQUENCE: 9

tatagtagaa accac                                                   15
```